(12) United States Patent
Connolly et al.

(10) Patent No.: US 6,342,370 B1
(45) Date of Patent: *Jan. 29, 2002

(54) HUMAN SLIT POLYPEPTIDE AND POLYNUCLEOTIDES ENCODING SAME

(75) Inventors: Timothy Connolly, Belmont, MA (US); Bhanu Rajput, New Carrollton, MD (US)

(73) Assignee: Osiris Therapeutics, Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/182,024

(22) Filed: Oct. 29, 1998

Related U.S. Application Data

(60) Provisional application No. 60/096,420, filed on Aug. 13, 1998, and provisional application No. 60/063,946, filed on Oct. 31, 1997.

(51) Int. Cl.[7] .......................... C12P 21/06; C12N 15/00
(52) U.S. Cl. .................. 435/69.1; 536/23.5; 435/6; 435/320.1; 435/325
(58) Field of Search .................. 435/6, 69.1, 320.1, 435/325; 536/23.5

(56) References Cited

U.S. PATENT DOCUMENTS 6,046,015 A  *  4/2000  Goodman et al. ........... 435/7.8

FOREIGN PATENT DOCUMENTS

| JP | 10-87699  | * | 4/1998 |
| JP | 11-18777  | * | 1/1999 |
| JP | 11-75846  | * | 1/1999 |
| WO | WO 92 10518 |   | 6/1992 |

OTHER PUBLICATIONS

Itoh, et al., "Cloning and expressions of three mammalian homologues of *Drosophila slit* suggest possible roles for Slit in the formation and maintenance of the nervous system," *Molecular Brain Research* 62:175–186 (1998).

Nakayama, et al., "Identification of High–Molecular–Weight Proteins with Multiple EGF–like Motifs by Motif–Trap Screening," *Genomics*, 51:27–34 (1998).

Hiller et al.: "The WashU–MerckEST Project 1997, AC AA96230" EMBL Database, Jul. 3, 1997, XP002097995.

AC AA506521 EMBL Database, Jul. 4, 1997, XP002097996 Heidelberg.

Rothberg J. et al.: "Slit: An Extracellular Protein Necessary for Development of Midline Glia and Commissural Axon Pathways Contains Both EGF and LRR Domains" Genes & Development, vol. 4, No. 12a, Dec. 1990, pp. 2169–2187, XP002097997.

Database WPI, Section Ch, Week 9824, Derwent Publications Ltd., London, GB; Class C07, p. 45, AN 98–267127 XP002097999 & JP 10 087699 A (Asahi Kasei Kogyo KK), Apr. 7, 1998.

AB011531, GenBank, Aug. 22, 1998.*
AB017169, GenBank, Feb. 6, 1999.*
Ab011538, GenBank, Aug. 22, 1998.*

* cited by examiner

Primary Examiner—Marianne P. Allen
(74) Attorney, Agent, or Firm—Elliot M. Olstein; Alan J. Grant

(57) ABSTRACT

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human slit polypeptides. The invention also relates to identifying mesenchymal stem cells (MSCs) or other cells comprising such polypeptides or polynucleotides that encode the polypeptides.

9 Claims, 22 Drawing Sheets

FIG. 2

Figure 1:
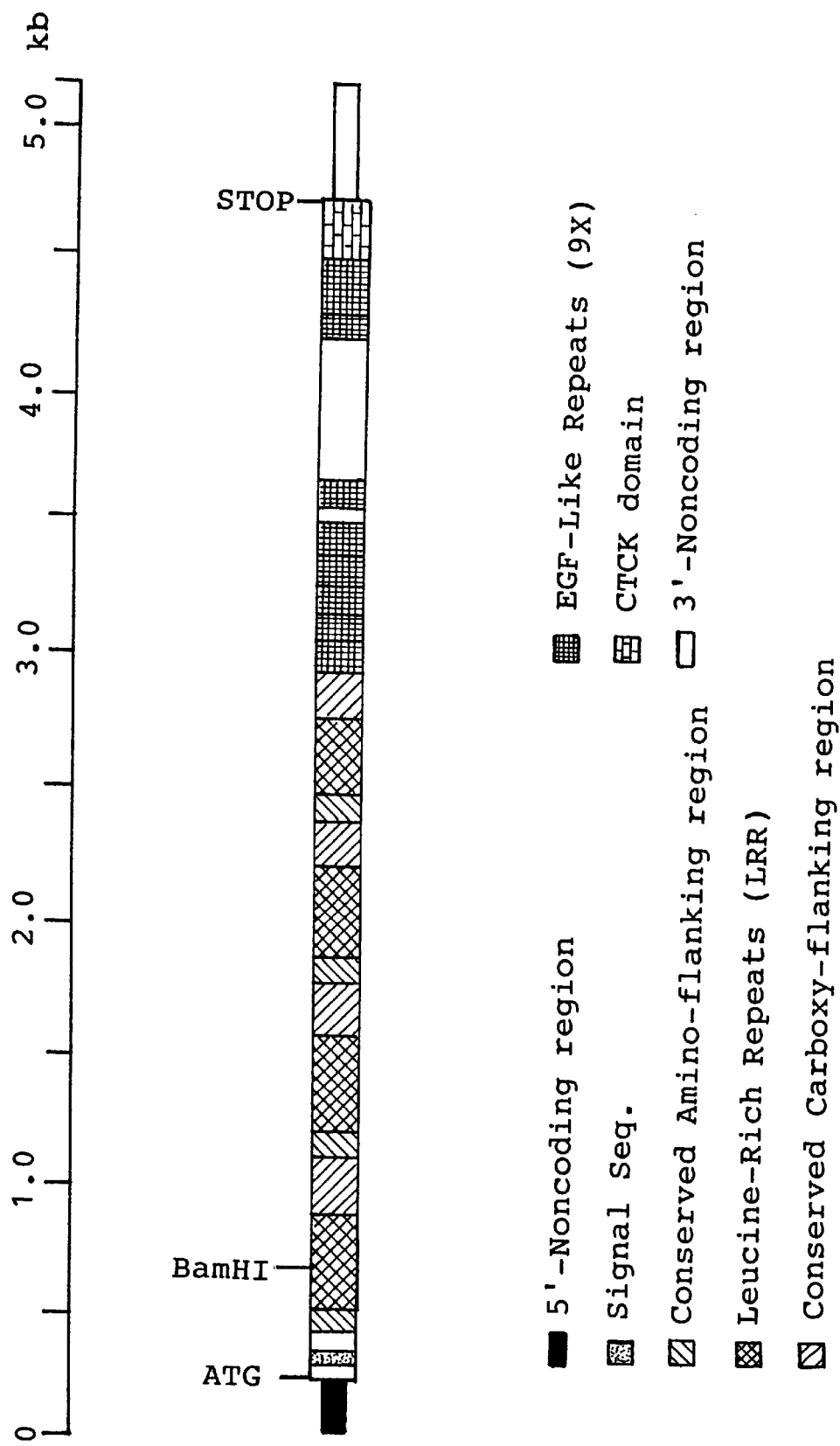

| FIG.2A | FIG.2B |
|---|---|
| FIG.2C | FIG.2D |
| FIG.2E | FIG.2F |
| FIG.2G | FIG.2H |
| FIG.2I | FIG.2J |
| FIG.2K | FIG.2L |
| FIG.2M | FIG.2N |

FIG. 2A

```
1                             GCCGGCCCCGCCGATGGAGCT
62            GCCCGCGCCCCGTGCGCCTGAGCACCGAGCTCGCCCTC
141           GCTCCCCGCGCGCCTCCTCGGGCTCCACGCGTCTTGCCC

220       ATG GCC CCC GGG TGG GCA GGG GTC GGC GCC
1         Met ala pro gly trp ala gly val gly ala 280       GCG CTG GCG AGC GTC CTG AGT GGG CCT CCA
21        ala leu ala ser val leu ser gly pro pro 340       TCC GCT GCC AGC GTG GAC TGC CAC GGG CTG
41        ser ala ala ser val asp cys his gly leu 400       CGC AAC GCT GAG CGC CTT GAC CTG GAC AGA
61        arg asn ala glu arg leu asp leu asp arg 460       TTC GCT GGG CTC AAG AAC CTC CGA GTC TTG
81        phe ala gly leu lys asn leu arg val leu 520       GAG AGA GGC GCC TTC CAG GAC CTG AAG CAG
101       glu arg gly ala phe gln asp leu lys gln 580       CTG CAA GTC CTT CCA GAA TTG CTT TTC CAG
121       leu gln val leu pro glu leu leu phe gln 640       AGT GAA AAC CAG ATC CAG GGG ATC CCG AGG
141       ser glu asn gln ile gln gly ile pro arg 700       AAC CTG CAA CTG GAC AAC AAC CAC ATC AGC
161       asn leu gln leu asp asn asn his ile ser 760       CGC GAT TTG GAG ATC CTT ACC CTC AAC AAC
181       arg asp leu glu ile leu thr leu asn asn 820       TTC AAC CAC ATG CCG AAG ATC CGA ACT CTG
201       phe asn his met pro lys ile arg thr leu
```

MATCH WITH FIG. 2B

MATCH WITH FIG. 2C

FIG. 2B

GCTGTTGCTGCCGCCGCCGCCTCCCGGAGCGCCCCGCTCC
CTCCGCGCTAACTCCGCCGCCCGCTCCCCAGGCCGCCCGC
CGCAGAGGCAGCCTCCTCCAGGAGCGGGGCCCTGCACACC

MATCH WITH FIG. 2A

| GCC | GTG | CGC | GCC | CGC | CTG | GCG | CTG | GCC | TTG |
|-----|-----|-----|-----|-----|-----|-----|-----|-----|-----|
| ala | val | arg | ala | arg | leu | ala | leu | ala | leu |

| GCC | GTC | GCC | TGC | CCC | ACC | AAG | TGT | ACC | TGC |
| ala | val | ala/cys | pro | thr | lys | cys | thr | cys |

| GGC | CTC | CGC | GCG | GTT | CCT | CGG | GGC | ATC | CCC |
| gly | leu | arg | ala | val | pro | arg | gly | ile | pro |

| AAT | AAT | ATC | ACC | AGG | ATC | ACC | AAG | ATG | GAC |
| asn | asn | ile | thr | arg | ile | thr | lys | met | asp |

| CAT | CTG | GAA | GAC | AAC | CAG | GTC | AGC | GTC | ATC |
| his | leu | glu | asp | asn | gln | val | ser | val | ile |

| CTA | GAG | CGA | CTG | CGC | CTG | AAC | AAG | AAT | AAG |
| leu | glu | arg | leu | arg | leu | asn | lys | asn | lys |

| AGC | ACG | CCG | AAG | CTC | ACC | AGA | CTA | GAT | TTG |
| ser | thr | pro | lys | leu | thr | arg | leu | asp | leu |

| AAG | GCG | TTC | CGC | GGC | ATC | ACC | GAT | GTG | AAG |
| lys | ala | phe | arg | gly | ile | thr | asp | val | lys |

| TGC | ATT | GAA | GAT | GGA | GCC | TTC | CGA | GCG | CTG |
| cys | ile | glu | asp | gly | ala | phe | arg | ala | leu |

| AAC | AAC | ATC | AGT | CGC | ATC | CTG | GTC | ACC | AGC |
| asn | asn | ile | ser | arg | ile | leu | val | thr | ser |

| CGC | CTC | CAC | TCC | AAC | CAC | CTG | TAC | TGC | GAC |
| arg | leu | his | ser | asn | his | leu | tyr | cys | asp |

MATCH WITH FIG. 2D

MATCH WITH FIG. 2A  FIG. 2C

```
880   TGC CAC CTG GCC TGG CTC TCG GAT TGG CTG
221   cys his leu ala trp leu ser asp trp leu 940   CTC TGC ATG GCT CCT GTG CAT TTG AGG GGC
241   leu cys met ala pro val his leu arg gly 1000  TAC GTG TGC CCA GCC CCC CAC TCG GAG CCC
261   tyr val cys pro ala pro his ser glu pro 1060  CCT TCG CCC TGC ACG TGC AGC AAT AAC ATC
281   pro ser pro cys thr cys ser asn asn ile 1120  ATT CCT GCC AAT TTG CCG GAG GGC ATC GTC
301   ile pro ala asn leu pro glu gly ile val 1180  GCC ATC CCT GCA GGA GCC TTC ACC CAG TAC
321   ala ile pro ala gly ala phe thr gln tyr 1240  AAT CAG ATA TCG GAT ATT GCT CCA GAT GCC
341   asn gln ile ser asp ile ala pro asp ala 1300  GTC CTG TAT GGG AAC AAG ATC ACC GAG ATT
361   val leu tyr gly asn lys ile thr glu ile 1360  CTA CAG CTG CTC CTC CTC AAT GCC AAC AAG
381   leu gln leu leu leu leu asn ala asn lys 1420  GAC CTG CAG AAC CTC AAC TTG CTC TCC CTG
401   asp leu gln asn leu asn leu leu ser leu 1480  GGG CTC TTC GCC CCT CTG CAG TCC ATC CAG
421   gly leu phe ala pro leu gln ser ile gln 1540  TGC GAC TGC CAC TTG AAG TGG CTG GCC GAC
441   cys asp cys his leu lys trp leu ala asp
```

MATCH WITH FIG. 2D

MATCH WITH FIG. 2E

FIG. 2D    MATCH WITH FIG. 2B

```
CGA CAG CGA CGG ACA GTT GGC CAG TTC ACA
arg gln arg arg thr val gly gln phe thr TTC AAC GTG GCG GAT GTG CAG AAG AAG GAG
phe asn val ala asp val gln lys lys glu CCA TCC TGC AAT GCC AAC TCC ATC TCC TGC
pro ser cys asn ala asn ser ile ser cys GTG GAC TGT CGA GGA AAG GGC TTG ATG GAG
val asp cys arg gly lys gly leu met glu GAA ATA CGC CTA GAA CAG AAC TCC ATC AAA
glu ile arg leu glu gln asn ser ile lys AAG AAA CTG AAG CGA ATA GAC ATC AGC AAG
lys lys leu lys arg ile asp ile ser lys TTC CAG GGC CTG AAA TCA CTC ACA TCG CTG
phe gln gly leu lys ser leu thr ser leu GCC AAG GGA CTG TTT GAT GGG CTG GTG TCC
ala lys gly leu phe asp gly leu val ser ATC AAC TGC CTG CGG GTG AAC ACG TTT CAG
ile asn cys leu arg val asn thr phe gln TAT GAC AAC AAG CTG CAG ACC ATC AGC AAG
tyr asp asn lys leu gln thr ile ser lys ACA CTC CAC TTA GCC CAA AAC CCA TTT GTG
thr leu his leu ala gln asn pro phe val TAC CTC CAG GAC AAC CCC ATC GAG ACA AGC
tyr leu gln asp asn pro ile glu thr ser
```

MATCH With FIG. 2F

MATCH WITH FIG. 2C

FIG. 2E

```
1600   GGG GCC CGC TGC AGC AGC CCG CGC CGA CTC
 461   gly ala arg cys ser ser pro arg arg leu 1660   AAG AAG TTC CGC TGC TCA GGC TCC GAG GAT
 481   lys lys phe arg cys ser gly ser glu asp 1720   ATG GAC CTC GTG TGC CCC GAG AAG TGT CGC
 501   met asp leu val cys pro glu lys cys arg 1780   CAG AAG CTG GTC CGC ATC CCA AGC CAC CTC
 521   gln lys leu val arg ile pro ser his leu 1840   GAC AAT GAG GTA TCT GTT CTG GAG GCC ACT
 541   asp asn glu val ser val leu glu ala thr 1900   AAA ATA AAT CTG AGT AAC AAT AAG ATC AAG
 561   lys ile asn leu ser asn asn lys ile lys 1960   GCC AGC GTG CAG GAG CTG ATG CTG ACA GGG
 581   ala ser val gln glu leu met leu thr gly 2020   TTC CGT GGC CTC AGT GGC CTC AAA ACC TTG
 601   phe arg gly leu ser gly leu lys thr leu 2080   AGT AAT GAC ACC TTT GCC GGC CTG AGT TCG
 621   ser asn asp thr phe ala gly leu ser ser 2140   ATC ACC ACC ATC ACC CCT GGG GCC TTC ACC
 641   ile thr thr ile thr pro gly ala phe thr 2200   CTG TCC AAC CCC TTC AAC TGC AAC TGC CAC
 661   leu ser asn pro phe asn cys asn cys his 2260   AGG CGG ATC GTC AGT GGG AAC CCT AGG TGC
 681   arg arg ile val ser gly asn pro arg cys
```

MATCH WITH FIG. 2G

MATCH WITH FIG. 2F

FIG. 2F

MATCH WITH FIG. 2D

```
GCC AAC AAG CGC ATC AGC CAG ATC AAG AGC
ala asn lys arg ile ser gln ile lys ser TAC CGC AGC AGG TTC AGC AGC GAG TGC TTC
tyr arg ser arg phe ser ser glu cys phe TGT GAG GGC ACG ATT GTG GAC TGC TCC AAC
cys glu gly thr ile val asp cys ser asn CCT GAA TAT GTC ACC GAC CTG CGA CTG AAT
pro glu tyr val thr asp leu arg leu asn GGC ATC TTC AAG AAG TTG CCC AAC CTG CGG
gly ile phe lys lys leu pro asn leu arg GAG GTG CGA GAG GGA GCT TTC GAT GGA GCA
glu val arg glu gly ala phe asp gly ala AAC CAG CTG GAG ACC GTG CAC GGG CGC GTG
asn gln leu glu thr val his gly arg val ATG CTG AGG AGT AAC TTG ATC AGC TGT GTG
met leu arg ser asn leu ile ser cys val GTG AGA CTG CTG TCC CTC TAT GAC AAT CGG
val arg leu leu ser leu tyr asp asn arg ACG CTT GTC TCC CTG TCC ACC ATA AAC CTC
thr leu val ser leu ser thr ile asn leu CTG GCC TGG CTC GGC AAG TGG TTG AGG AAG
leu ala trp leu gly lys trp leu arg lys CAG AAG CCA TTT TTC CTC AAG GAG ATC CCC
gln lys pro phe phe leu lys glu ile pro
```

MATCH WITH FIG. 2E

MATCH WITH FIG. 2H

MATCH WITH FIG. 2E

FIG. 2G

```
2320    ATC CAG GAT GTG GCC ATC CAG GAC TTC ACC
 701    ile gln asp val ala ile gln asp phe thr 2380    CTG AGC CCG CGC TGC CCG GAG CAG TGC ACC
 721    leu ser pro arg cys pro glu gln cys thr 2440    AAG GGG CTC CGC GCC CTC CCC AGA GGC ATG
 741    lys gly leu arg ala leu pro arg gly met 2500    GGA AAC CAC CTA ACA GCC GTG CCC AGA GAG
 761    gly asn his leu thr ala val pro arg glu 2560    GAC CTG AGC AAC AAC AGC ATC AGC ATG CTG
 781    asp leu ser asn asn ser ile ser met leu 2620    CTC TCC ACT CTG ATC CTG AGC TAC AAC CGG
 801    leu ser thr leu ile leu ser tyr asn arg 2680    GGG CTG CGG TCC CTG CGA GTG CTA ACC CTC
 821    gly leu arg ser leu arg val leu thr leu 2740    GGC TCC TTC AAC GAC CTC ACA TCT CTT TCC
 841    gly ser phe asn asp leu thr ser leu ser 2800    TGT GAC TGC AGT CTT CGG TGG CTG TCG GAG
 861    cys asp cys ser leu arg trp leu ser glu 2860    ATC GCC CGC TGC AGT AGC CCT GAG CCC ATG
 881    ile ala arg cys ser ser pro glu pro met 2920    CAC CGC TTC CAG TGC AAA GGG CCA GTG GAC
 901    his arg phe gln cys lys gly pro val asp 2980    CTC TCC AGC CCG TGC AAG AAT AAC GGG ACA
 921    leu ser ser pro cys lys asn asn gly thr
```

MATCH WITH FIG. 2H

MATCH WITH FIG. 2I

MATCH WITH FIG. 2F

FIG. 2H

```
TGT GAT GGC AAC GAG GAG AGT AGC TGC CAG
cys asp gly asn glu glu ser ser cys gln TGT ATG GAG ACA GTG GTG CGA TGC AGC AAC
cys met glu thr val val arg cys ser asn CCC AAG GAT GTG ACC GAG CTG TAC CTG GAA
pro lys asp val thr glu leu tyr leu glu CTG TCC GCC CTC CGA CAC CTG ACG CTT ATT
leu ser ala leu arg his leu thr leu ile ACC AAT TAC ACC TTC AGT AAC ATG TCT CAC
thr asn tyr thr phe ser asn met ser his CTG AGG TGC ATC CCC GTC CAC GCC TTC AAC
leu arg cys ile pro val his ala phe asn CAT GGC AAT GAC ATT TCC AGC GTT CCT GAA
his gly asn asp ile ser ser val pro glu CAT CTG GCG CTG GGA ACC AAC CCA CTC CAC
his leu ala leu gly thr asn pro leu his TGG GTG AAG GCG GGG TAC AAG GAG CCT GGC
trp val lys ala gly tyr lys glu pro gly GCT GAC AGG CTC CTG CTC ACC ACC CCA ACC
ala asp arg leu leu leu thr thr pro thr ATC AAC ATT GTG GCC AAA TGC AAT GCC TGC
ile asn ile val ala lys cys asn ala cys TGC ACC CAG GAC CCT GTG GAG CTG TAC CGC
cys thr gln asp pro val glu leu tyr arg
```

MATCH WITH FIG. 2G

MATCH WITH FIG. 2J

FIG. 2I

MATCH WITH FIG. 2G

```
3040    TGT GCC TGC CCC TAC AGC TAC AAG GGC AAG
941     cys ala cys pro tyr ser tyr lys gly lys 3100    CAG AAC CCC TGT CAG CAT GGA GGC ACC TGC
961     gln asn pro cys gln his gly gly thr cys 3160    AGC TGC TCC TGC CCT CTG GGC TTT GAG GGG
981     ser cys ser cys pro leu gly phe glu gly 3220    GAG GAC AAC GAC TGC GAA AAC AAT GCC ACC
1001    glu asp asn asp cys glu asn asn ala thr 3280    ATC TGT CCG CCT AAC TAC ACA GGT GAG CTA
1021    ile cys pro pro asn tyr thr gly glu leu 3340    GAG CTG AAC CTC TGT CAG CAT GAG GCC AAG
1041    glu leu asn leu cys gln his glu ala lys 3400    GAG TGT GTC CCT GGC TAC AGC GGG AAG CTC
1061    glu cys val pro gly tyr ser gly lys leu 3460    CAC AAG TGC CGC CAC GGG GCC CAG TGC GTG
1081    his lys cys arg his gly ala gln cys val 3520    CCC CAG GGC TTC AGT GGA CCC TTC TGT GAA
1101    pro gln gly phe ser gly pro phe cys glu 3580    AGC CCA TGC GAC CAG TAC GAG TGC CAG AAC
1121    ser pro cys asp gln tyr glu cys gln asn 3640    CCC ACC TGC CGC TGC CCA CCA GGC TTC GCC
1141    pro thr cys arg cys pro pro gly phe ala 3700    AAC TTC GTG GGC AAA GAC TCC TAC GTG GAA
1161    asn phe val gly lys asp ser tyr val glu
```

MATCH WITH FIG. 2J

MATCH WITH FIG. 2K

MATCH WITH FIG. 2H  FIG. 2J

```
GAC TGC ACT GTG CCC ATC AAC ACC TGC ATC
asp cys thr val pro ile asn thr cys ile CAC CTG AGT GAC AGC CAC AAG GAT GGG TTC
his leu ser asp ser his lys asp gly phe CAG CGG TGT GAG ATC AAC CCA GAT GAC TGT
gln arg cys glu ile asn pro asp asp cys TGC GTG GAC GGG ATC AAC AAC TAC GTG TGT
cys val asp gly ile asn asn tyr val cys TGC GAC GAG GTG ATT GAC CAC TGT GTG CCT
cys asp glu val ile asp his cys val pro TGC ATC CCC GTG GAC AAA GGA TTC AGC TGC
cys ile pro leu asp lys gly phe ser cys TGT GAG ACA GAC AAT GAT GAC TGT GTG GCC
cys glu thr asp asn asp asp cys val ala GAC ACA ATC AAT GGC TAC ACA TGC ACC TGC
asp thr ile asn gly tyr thr cys thr cys CAC CCC CCA CCC ATG GTC CTA CTG CAG ACC
his pro pro pro met val leu leu gln thr GGG GCC CAG TGC ATC GTG GTG CAG CAG GAG
gly ala gln cys ile val val gln gln glu GGC CCC AGA TGC GAG AAG CTC ATC ACT GTC
gly pro arg cys glu lys leu ile thr val CTG GCC TCC GCC AAG GTC CGA CCC CAG GCC
leu ala ser ala lys val arg pro gln ala
```

MATCH WITH FIG. 2L

MATCH WITH FIG. 2I

FIG. 2K

MATCH WITH FIG. 2I

```
3760   AAC ATC TCC CTG CAG GTG GCC ACT GAC AAG
1181   asn ile ser leu gln val ala thr asp lys 3820   AAT GAC CCC CTG GCA CTG GAG CTG TAC CAG
1201   asn asp pro leu ala leu glu leu tyr gln 3880   AGT TCC CCT CCA ACC ACA GTG TAC AGT GTG
1221   ser ser pro pro thr thr val tyr ser val 3940   GTG GAG CTG GTG ACG CTA AAC CAG ACC CTG
1241   val glu leu val thr leu asn gln thr leu 4000   AGC CTG GGG AAG CTC CAG AAG CAG CCA GCA
1261   ser leu gly lys leu gln lys gln pro ala 4060   GGC ATC CCC ACC TCC ACC GGC CTC TCC GCC
1281   gly ile pro thr ser thr gly leu ser ala 4120   GGC TTC CAC GGA TGC ATC CAT GAG GTG CGC
1301   gly phe his gly cys ile his glu val arg 4180   CTC CCA CCA CAG TCC CTG GGG GTG TCA CCA
1321   leu pro pro gln ser leu gly val ser pro 4240   GGC CTG TGC CGC TCC GTG GAG AAG GAC AGC
1341   gly leu cys arg ser val glu lys asp ser 4300   GGC CCA CTC TGC GAC CAG GAG GCC CGG GAC
1361   gly pro leu cys asp gln glu ala arg asp 4360   AAA TGT GTG GCA ACT GGG ACC TCA TAC ATG
1381   lys cys val ala thr gly thr ser tyr met 4420   TTG TGT GAC AAC AAG AAT GAC TCT GCC AAT
1401   leu cys asp asn lys asn asp ser ala asn
```

MATCH WITH FIG. 2M

MATCH WITH FIG. 2L

FIG. 2L

MATCH WITH FIG. 2J

```
GAC AAC GGC ATC CTT CTC TAC AAA GGA GAC
asp asn gly ile leu leu tyr lys gly asp GGC CAC GTG CGG CTG GTC TAT GAC AGC CTG
gly his val arg leu val tyr asp ser leu GAG ACA GTG AAT GAT GGG CAG TTT CAC AGT
glu thr val asn asp gly gln phe his ser AAC CTA GTA GTG GAC AAA GGA ACT CCA AAG
asn leu val val asp lys gly thr pro lys GTG GGC ATC AAC AGC CCC CTC TAC CTT GGA
val gly ile asn ser pro leu tyr leu gly TTG CGC CAG GGC ACG GAC CGG CCT CTA GGC
leu arg gln gly thr asp arg pro leu gly ATC AAC AAC GAG CTG CAG GAC TTC AAG GCC
ile asn asn glu leu gln asp phe lys ala GGC TGC AAG TCC TGC ACC GTG TGC AAG CAC
gly cys lys ser cys thr val cys lys his GTG GTG TGC GAG TGC CGC CCA GGC TGG ACC
val val cys glu cys arg pro gly trp thr CCC TGC CTC GGC CAC AGA TGC CAC CAT GGA
pro cys leu gly his arg cys his his gly TGC AAG TGT GCC GAG GGC TAT GGA GGG GAC
cys lys cys ala glu gly tyr gly gly asp GCC TGC TCA GCC TTC AAG TGT CAC CAT GGG
ala cys ser ala phe lys cys his his gly
```

MATCH WITH FIG. 2N

MATCH WITH FIG. 2K

FIG. 2M

MATCH WITH FIG. 2K

```
4480    CAG TGC CAC ATC TCA GAC CAA GGG GAG CCC
1421    gln cys his ile ser asp gln gly glu pro 4540    GAG CAC TGC CAA CAA GAG AAT CCG TGC CTG
1441    glu his cys gln gln glu asn pro cys leu 4600    CAG AAA GGT TAT GCA TCA TGT GCC ACA GCC
1461    gln lys gly tyr ala ser cys ala thr ala 4660    GGC TGT GGG CCC CAG TGC TGC CAG CCC ACC
1481    gly cys gly pro gln cys cys gln pro thr 4720    TGC ACG GAC GGC TCC TCG TTT GTA GAA GAG
1501    cys thr asp gly ser ser phe val glu glu 4780    GCG TGT TCC TAA GCCCCTGCCCGCCTGCCTGCCACCT
1521    ala cys ser Stop 4855    GGACCCCCTGGTGATTCAGCATGAAGGAAATGAAGCTGGAG
4934    AAATAAACAAAAAATAGAACTTATTTTTATTATGGAAAGTG
5013    TCTGCGTATATGTACCATATAGTGAGTTATTTTTACCAAGT
5092    TTTAAAAATTTAAGAAAAAAATAGACTAATAAAAATGCTTT
5171    GAGGAA
```

MATCH WITH FIG. 2N

FIG. 2N

MATCH WITH FIG. 2L

MATCH WITH FIG. 2M

```
TAC TGC CTG TGC CAG CCC GGC TTT AGC GGC
tyr cys leu cys gln pro gly phe ser gly GGA CAA GTA GTC CGA GAG GTG ATC CGC CGC
gly gln val val arg glu val ile arg arg TCC AAG GTG CCC ATC ATG GAA TGT CGT GGG
ser lys val pro ile met glu cys arg gly CGC AGC AAG CGG CGG AAA TAC GTC TTC CAG
arg ser lys arg arg lys tyr val phe gln GTG GAG AGA CAC TTA GAG TGC GGC TGC CTC
val glu arg his leu glu cys gly cys leu
```

CTCGGACTCCAGCTTGATGGAGTTGGGACAGCCATGTG

AGGAAGGTAAAGAAGAAGAGAATATTAAGTATATTGTA
ACTATTTTCATCTTTTATTATATAAATATATTACACCA
TTTGTGTTGTGTATTTGTTGTGTTTTTAAAAATAGCTG
AAAACAAAAGGATAAGAATAAAGAATGATAGCCTGTCT

FIG. 3A

```
hSlit  -MAPGWAGVG-AAVRARLALALALASVLSGPPAV-ACPTKCTCSAASVDCHGLGLR--AV   55
dSlit  MAAPSRTTLMPPPFERLQLRLLILPILLLRHDAVHAEPYSGGFGSSAVSSGGLGSVGIHI   60
        *  .:  .: ...:*:*       * *** hSlit  PRG-----I-----PRNAERLDLDRNNITR-ITKMDFAGLKNLRVLHLEDNQVSVIERGAF  105
dSlit  PGGGVGVITEARCPRVCSCTGLNVDCSHRGLTSVPRKISADVERLELQGNNLTVIYETDF  120
        * *   *      **.    :*:: :*  *:.**:*:*:.**   **:*.**  . .

hSlit  QDLKQLERLRLNKNKLQVLPELLFQSTPKLTRLDLSENQIQGIPRKAFRGITDVKNLQLD  165
dSlit  QRLTKLRMLQLTDNQIHTIERNSFQDLVSLERLDISNNVITTVGRRVFEKGAQSLRSLQLD  180
        * *  **  * :::: :: *.:  :  * ***.:*: * : * *.*  *  .**. ****

hSlit  NNHISCIEDGAFRALRDLEILTLNNNISRILVTSFNHMPKIRTLRLHSNHLYCDCHLAW  225
dSlit  NNQITCLDEHAFKGLVELEILTLNNNNLTSLPHNIFGGLRLALRLSDNPFACDCHLSW  240
        **:*:*:::.**:.* :*:*******  .: ::  .:  ::* *.*  ..*****:* hSlit  LSDWLRQRRTVGQFTLCMAPVHLRGFNVADVQKKEYVCP--APHSEPPSCNANSISCPSP  283
dSlit  LSRFLRSATRLAPYTRCQSPSQLKGQNVADLHDQEFKCSGLTEHA-PMECGA-ENSCPHP  298
        . .   .. :* * :*. *:*:.:***:: ::::*.   * *  *.*.  ***.* hSlit  CTCSNNIVDCRGKGLMEIPANLPEGIVEIRLEQNSIKAIPAGAFTQYKKLKRIDISKNQI  343
dSlit  CRCADGIVDCREKSLTSVPVTLPDDTTDVRLEQNFITELPPKSFSSFRRLRRIDLSNNNI  358
        * *:  ******..  .:*..**:.*.::*****.*  :*....:..::*:***:*:*
```

FIG. 3B

```
hSlit  SDIAPDAFQGLKSLTSLVLYGNKITEIAKGLFDGLVSLQLLLNANKINCLRVNTFQDLQ  403
dSlit  SRIAHDALSGLKQLTTLVLYGNKIKDLPSGVFKGLGSLRLLLLNANEISCIRKDAFRDLH  418
          *  **  ;***  *  *******   *  *;   ::   :: ;* +:

hSlit  NLNLLSLYDNKLQTISKGLFAPLQSIQTLHLAQNPFVCDCHLKWLADYLQDNPIETSGAR  463
dSlit  SLSLLSLYDNNIQSLANGTFDAMKSMKTVHLAKNPFICDCNLRWLADYLHKNPIETSGAR  478
        * . ******  :*:   *:   *    : *:**** :******* hSlit  CSSPRRLANKRISQIKSKKFRCSGSEDYRSRFSSECFMDLVCPEKCRCEGTIVDCSNQKL  523
dSlit  CESPKRMHRRRIESLREEKFKCSWGE-LRMKLSGECRMDSDCPAMCHCEGTTVDCTGRRL  537
       * **:*:  ::  . :**  *:  *  * ** *  ** * ***.* . :* hSlit  VRIPSHLPEYVTDLRLNDNEVSVLEATGIFKKLPNLRKINLSNNKIKEVREGAFDGAASV  583
dSlit  KEIPRDIPLHTTELLLNDNELGRISSDGLFGRLPHLVKLELKRNQLTGIEPNAFEGASHI  597
         **.  *   * :****:  :   *:* :**.* *:::*.*:    : * ** **::

hSlit  QELMLTGNQLETVHGRVFRGLSGLKTLMLRSNLISCVSNDTFAGLSSVRLLSLYDNRITT  643
dSlit  QELQL-G---E-----------------NKIKEISNKMFLGLHQLKTLNLYDNQISC    633
       *** * *   *                 *   :**  * **.  :* *:****:*:

hSlit  ITPGAFTTLVSLSTINLLSNPFNCNCHLAWLGKWLRKRRIVSGNPRCQKPFFLKEIPIQD  703
dSlit  VMPGSFEHLNSLTSLNLASNPFNCNCHLAWFAECVRKKSLNGGAARCGAPSKVRDVQIKD  693
       : **:*  * **:::**:*********** .  :**:.  . * * * . *:: * **
```

FIG. 3C

```
hSlit  VAIQDFTCDGNEESSCQLSPRCPEQCTCMETVVRCSNKGLRALPRGMPKDVTELYLEGNH 763
dSlit  LPHSEFKCS.SENSEGCLGDGYCPPSCTCTGTVVACSRNQLKEIPRGIPAETSELYLESNE 753
       : . .:. :*:**   * :  *  : ***  ** . *  :*   ***. *:. .

hSlit  LTAVPRE-LSALRHLTLIDLSNNSISMLTNYTFSNMSHLSTLILSYNRLRCIPVHAFNGL 822
dSlit  IEQIHYERIRHLRSLTRLDLSNNQITILSNYTFANLTKLSTLIISYNKLQCLQRHALSGL 813
       :  :  *  : ** ** :****.*: :*:****:*  :.****:**::*:*:  .: **

hSlit  RSLRVLTLHGNDISSVPEGSFNDLTSLSHLALGTNPLHCDCSLRWLSEWVKAGYKEPGIA 882
dSlit  NNLRVVSLHGNRISMLPEGSFEDLKSLTHIALGSNPLYCDCGLKWFSDWIKLDYVEPGIA 873
       .:*:: .:**:.**:*:*:* ***.*:*:*:*:* .*:***** hSlit  RCSSPEPMADRLLLTTPTHRFQCKGPVDINIVAKCNACLSSPCKNNGTCTQDPVELYRCA 942
dSlit  RCAEPEQMKDKLILSTPSSSFVCRGRVRNDILAKCNACFEQPCQNQAQCVALPQREYQCL 933
       **:.**.*.*:*:*:**: .*:*:* *.::****:**..**:*:..*..**::*:**:

hSlit  CPYSYKGKDCTVPINTCIQNPCQHGGTCHLSDSHKDGFSCSCPLGFEGQRCEINPDDCE- 1001
dSlit  CQPGYHGDCKHCEFMIDACYGNPCRNNATCTVLE--EGRFSCQCAPGYTGARCETNIDDCLG 991
       *   *:* :*.   :  *  :.***:... *.*.   *** *.** *.:**:*.**

hSlit  DNDCENNATCVDGINNYVCICPPNYTGELCDEVIDHCVPELNLCQHEAKCIPLDKGFSCE 1061
dSlit  EIKCQNNATCIDGVESYKCECQPGFSGEFCDTKIQFCSPEFNPCANGAKCMDHFTHYSCD 1051
       : . *:****:**::.* *:* *:.**:**.. : * .*:*:*  .*** ::* :**
```

FIG. 3D

```
hSlit  CVPGYSGKLCETDN-DDCVAHKCRHGAQCVDTINGYTCTCPQGFSGPFCE-H-PPPMVLL1118
dSlit  CQAGFHGTNC-TDNIDDCQNHMCQNGGTCVDGINDYQCRCPDDYTGKYCEGHNMISMMYP1110
        *  . *:  **  * * *** *:  * * *    * ***     ::  * hSlit  QTSPCDQYECQNGAQCIV--VQ-QEPTCRCPPGFAGPRCEKLITVNFVGKDSYVELASAKI1175
dSlit  QTSPCQNHECKHGV-CFQPNAQGSDYLCRCHPGYTGKWCEYLTSISFVHNNSFVELEPLR1169
       *****:::** :*   .:   * :  ** ** * *:  ** *:*. :.:*:.:.:****   :

hSlit  VRPQANISLQVATDKDNGILLLYKGDNDPLALELYQGHVRLVYDSLSSPPTTVYSVETVND1235
dSlit  TRPEANVTIVFSSAEQNGILMYDGQDAHLAVELFNGRIRVSYDVGNHPVSTMYSFEMVAD1229
          :: .::::** :  *.:* * ****:* : * **.  ..* ****.* ** hSlit  GQFHSVELVTLNQTLNLVVDKGTPKSLGKLQKQPAVGINSPLYLGGIPTSTGLSALRQGT1295
dSlit  GKYHAVELLAIKKNFTLRVDRGLARSIINEGSNDYLKLTTPMFLGGLPVDPAQQAYKNWQ1289
       *::*:***::::::  ** ** :   :.:   ..  *::  *.* ***:* .  :  :

hSlit  DRPLGGFHGCIHEVRINNELQDFKALPPQSLGVSPGCKSCTVCKHGLCRSVEKDSVVCEC1355
dSlit  IRNLTSFKGCMKEVWINHKLVDFGNAQRQQK-ITPG---CALLE-GEQQEEDD---EQD1341
        * *..*:**::** **::* ** :.  ::  : *.   **  : *::::*
```

FIG. 3E

```
hSlit  RPGWTGPLCDQEARDPCLGHRCHHG-KCVATGTSYMCKCAEGYGGDLCDNKNDSANACSA 1414
dSlit  FMDET-PHIKEEPVDPCLENKCRRGSRCVPNSNAR-----DGY----------QC--1380
            *   .:*.  ****  ::  ::::*  :..:.:         :        * hSlit  FKCHHGQCHISDQGEPYCLCQPGFSGEH-CQQENPCLGQVVREVIRRQKGYASCATASKV 1473
dSlit  -KCKHGQ-----RGR-YCDQGESTEPPTVTAASTCRKEQVREYY--TEN--DCRSRQPL 1429
        **::***          :*.  **      :.  *.:***:         :  ..

hSlit  PIMECRGGCGPQCCQPTRSKRRKYVFQCTDGSSFVEEVERHLECGCLA-CS 1523
dSlit  KYAKCVGGCGNQCCAAKIVRRRKVRMVCSNNRKYIKNLDIVRKCGCTKKCY 1480
          :*.****.:***.**:*  :::.  .::::::        :**** *
```

HUMAN SLIT POLYPEPTIDE AND POLYNUCLEOTIDES ENCODING SAME

This application claims the benefit of U.S. provisional Application Ser. Nos. 60/063,946, filed Oct. 31, 1997 and 60/096,420, filed Aug. 13, 1998, the disclosures of which are hereby incorporated by reference in their entirety.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human Slit polypeptides. The invention also relates to identifying mesenchymal stem cells (MSCs) or other cells comprising such polypeptides or polynucleotides that encode the polypeptides.

Proteins containing epidermal growth factor (EGF)-like sequences have been shown to play an important role in many aspects of eukaryotic cell control, acting as signals for proliferation, growth inhibition, and differentiation. A common feature of these proteins is their involvement in extracellular events and ligand-receptor interactions. In characterizing genomic DNA identified by cross-hybridization to the sequence coding for the tandem EGF repeats of Notch in Drosophila, a related gene sequence from an unlinked locus that also has EGF repeats was discovered. Isolation and characterization of it; showed a corresponce to the slit locus. Further characterization of the related gene sequence established that null mutations to it would result in disruptions of the embryonic central nervous system (CNS) (Rothberg et al. 1988) Thus, it was shown to be involved in neurogenesis.

The Drosophila slit protein contains two types of repeated amino acid sequences: leucine rich repeats ("LRR") and epidermal growth factor-like repeats ("EGF"). Its LRRs are arranged in four groups, each composed of four or five LRRs surrounded by conserved amino- and carboxy-flanking regions. The presence of both the LRRs and EGF-like repeats within a single protein make slit unusual in that such combination is not found in any other type of known protein. The absence of any potential transmembrane domains in a sequence having a typical signal sequence and two known extracellular-associated motifs suggests that the slit locus encodes a secreted extracellular protein. The LRR regions of the slit protein and such regions of related proteins participate in extracellular protein-protein interactions. Further, the EGF areas of the slit protein and such regions of related proteins participate in extracellular protein-protein reactions. Moreover, the slit protein is synthesized and secreted by midline glial cells can be come associated with axons. Among other functions, it influences the differentiation of midline cells from the neuroepithelium.

In accordance with one aspect of the present invention, there are provided novel polypeptides and polynucleotides, more particularly, the polypeptides of the present invention are of human origin and are found in human mesenchymal stem cells. MSCs are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines. The polypeptide is designated as human Slit. The human Slit polypeptide according to the present invention, as well as biologically active and diagnostically or therapeutically useful fragments, analogs and derivatives thereof, is of use in studing the culturing of MSCs and detection of their differentiation and development into multipotent cells.

In accordance with another aspect of the present invention, there are provided isolated nucleic acid molecules encoding such polypeptides, including mRNAs, cDNAs, genomic DNA as well as biologically active and diagnostically or therapeutically useful fragments, analogs and derivatives thereof.

In accordance with another aspect of the present invention there are provided nucleic acid probes comprising nucleic acid molecules of sufficient length to specifically hybridize to sequences of the present invention.

In accordance with yet a further aspect of the present invention, there is provided a process for producing such polypeptides by recombinant techniques which comprises culturing recombinant prokaryotic and/or eukaryotic host cells, containing a nucleic acid sequence of the present invention, under conditions promoting expression of said protein and subsequent recovery of said protein.

In accordance with yet a further aspect of the present invention, there is provided a process for utilizing such polypeptides, or polynucleotides encoding such polypeptides for identifying human MSCs by utilizing the polynucleotides as probes or by expressing the polypeptides encoded thereby, using such polypeptides to produce an antibody specific for one of the polypeptides and then utilizing the antibody to identify the MSCs. Further such polynucleotides, polypeptides and antibodies may be utilized to aid in the identification of MSCs from other species, as well as to investigate/identify MSC functions in humans or other species. In a preferred aspect of the invention, immunocyto-chemistry is utilized with an antibody specific for a polypeptide according to the invention as a means for monitoring the concentration of the polypeptide according to the invention in a culture solution. The MSCs of the culture may thus be subjected to purification procedures to remove differentiated cells and help to maintain the MSCs in culture.

In accordance with yet a further aspect of the present invention, there are provided antibodies against such polypeptides and a method of employing such antibodies to detect diseases related to an overexpression or under expression of a polypeptide compressing a polypeptide with an amino acid sequence according to the present invention. Such antibodies (or active fragments) may be utilized to monitor the growth of MSCs in a culture or to detect the location of tumors in the body.

In accordance with another aspect of the present invention there is provided a method of diagnosing a disease or a susceptibility to a disease related to a mutation in the nucleic acid sequences and the proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

FIG. 1 shows a schematic of the transcript for a cDNA clone that encodes the mature slit polypeptide. The various coding regions and repeats are identified by different types of cross-hatching as shown in the figure and identified by the legend below it.

FIG. 2 (parts 2A–2N) shows a cDNA sequence (SEQ ID. NO:1) that encodes the mature slit polypeptide (SEQ ID NO:2) of the present invention. Sequencing was performed using a 373 Automated DNA sequencer (Applied Biosystems, Inc.). Parts 2A–2N of the figure follow in sequence.

FIG. 3 (parts 3A–3E) is an illustration of amino acid sequence homology between the human slit polypeptide of the present invention (labelled as hSlit) SEQ ID. NO:2 and the Drosophila slit polypeptide (labelled as dSlit SEQ ID. NO:5). By aligning the two polypeptides in a manner that provides essentially the largest number of aligned identical amino acids over the complete comparison area of the two sequences, and dividing the total number of identical amino acids by the total length of the comparison area (counting the individual spaces or gaps as part of the comparison area), a 40% identity between the two amino acid sequences was observed. Standard one-letter abbreviations for amino acids are used. Parts 3A–3E of the figure follow in sequence.

Figure 4:
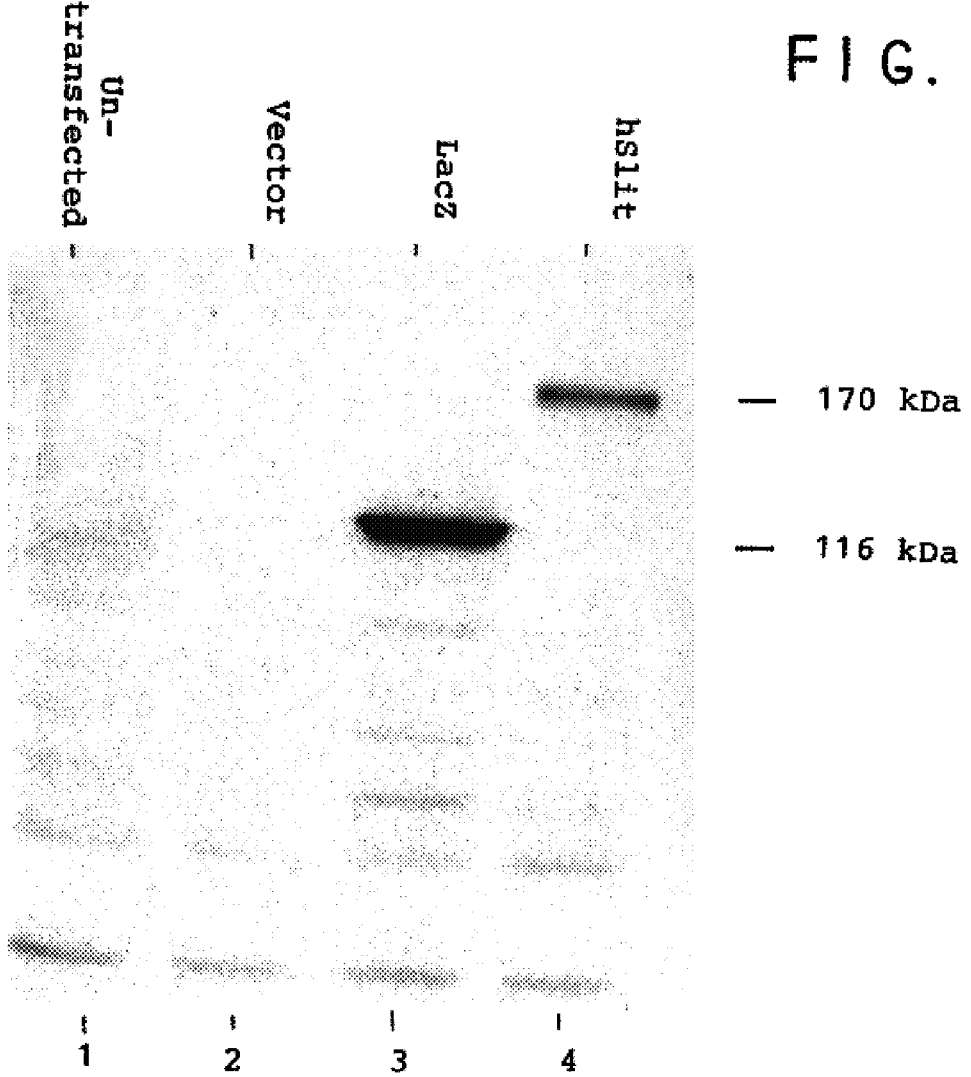

FIG. 4 shows a photograph of a protein blot from expression of hSlit in human embryonic kidney cell line, BOSC 23. Untransfected BOSC cells do not express hSlit. In FIG. 4, Lane 1 shows the results for untransfected BOSC cells; Lanes 2, 3 and 4, respectively show (2) BOSC cells transfected with pcDNA3.1/Myc-His/A vector, (3) pcDNA3.1/Myc-His/lacZ and (4) pcDNA3.1/Myc-His/hSlit cDNA.

In accordance with an aspect of the present invention, there are provided isolated nucleic acids (polynucleotides) which encode the mature polypeptides comprises the deduced amino acid sequences of SEQ ID NO:2. The mature forms of the slit polypeptide with and without an N-terminal methionine group (N-terminal methionine is the first amino acid of SEQ ID NO:2) are contemplated.

Polynucleotides encoding the polypeptide of the present invention have been isolated from a human MSC cDNA library. The polynucleotide contains an open reading frame encoding the human slit polypeptide. The protein exhibits a high degree of homology at the amino acid level to the Drosophila slit polypeptide with 40% identity (as shown in FIG. 3).

In accordance with a further aspect of the present invention the human slit gene sequence according to SEQ ID NO:1 or an appropriate fragment (full or partial length probes) may be utilized under stringent hybridization conditions to isolate from a cDNA library prepared from MSCs by procedures known in the art the cDNA encoding alleles of the mature slit polypeptide. Further, such full- or partial-length probes may be utilized to isolate genes (or cDNAs) encoding related polypeptides from non-human hosts under either stringent or highly-stringent hybridization conditions. Likewise the polypeptide having an amino acid sequence according to SEQ ID NO:2 or an immunogenic fragment may be utilized to produce antibodies specific for the polypeptide according to SEQ ID NO:2 and a fragment thereof. Such antibodies are in turn useful to detect the presence of such polypeptides when they are expressed by a clone or a transformed host cell to indicate the presence of the respective polynucleotides encoding such polypeptides.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may comprise an amino acid sequence identical to the coding sequence shown in FIG. 1 (SEQ ID NO:1) or may be a different coding sequence which coding sequence, as a result of the redundancy or degeneracy of the genetic code, encodes the same mature polypeptides comprising the polypeptide of SEQ. ID NO:2, the cDNA for which is shown in FIG. 1 (SEQ ID NO:1).

The polynucleotides which encode the mature polypeptides of the present invention comprise the polynucleotide sequence encoding the polypeptide of SEQ ID NO:2 and may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes coding sequence for the polypeptide and may also include additional coding and/or non-coding sequence such as introns.

The present invention further relates to variants of the hereinabove described polynucleotides which encode fragments, analogs and derivatives of the mature polypeptide comprising amino acid sequence shown in SEQ ID NO:2. The variant of the polynucleotides may be a naturally occurring allelic variant of the polynucleotides or a non-naturally occurring variant of the polynucleotides.

Further particularly preferred in this regard are polynucleotides encoding the human slit polypeptide variants, analogs, derivatives and fragments, and variants, analogs and derivatives of the fragments, which comprise the amino acid sequence of the polypeptide of SEQ ID NO:2 or of the deposit in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the human slit polypeptide. Also especially preferred in this regard are conservative substitutions. Most highly preferred are mature polypeptides comprising the amino acid sequence set forth in SEQ ID NO:2 or of the deposit, without substitutions.

Thus, the present invention includes polynucleotides encoding the same mature polypeptides comprising the polypeptide as set forth in SEQ ID NO:2 as well as variants of such polynucleotides which variants encode a fragment, derivative or analog of the polypeptides set forth in SEQ ID NO:2. Such polynucleotide variants include deletion variants, substitution variants and addition or insertion variants. Preferred are polynucleotide sequences comprising polynucleotide sequence variants of a starting polynucleotide sequence that are obtained by changing the starting polynucleotide sequence in at least one of the following ways (a) inserting at least one nucleotide into it, (b) deleting at least one nucleotide from it, (c) substituting at least one nucleotide for a nucleotide of it, or (d) a combination of at least two of (a), (b) and (c). The starting polynucleotide sequence that is changed to obtain variant polynucleotide sequences is a member selected from (i) the coding portion of SEQ ID NO:1 and (ii) a redundant sequence encoding the same mature polypeptide as the coding portion of SEQ ID NO:1. Each of the preferred variant polynucleotide sequences results from changing no more than a total of 10 percent of the coding sequence nucleotides of the starting polynucleotide sequence by such deletion, substitution, insertion or a combination thereof (i.e., not more than 10 nucleotides per 100 nucleotides). More preferred are variant polynucleotide sequences that result from changing no more than a total of 5 percent of the starting coding sequence nucleotides by deletion, insertion, substitution or a combination thereof. Even more preferred are variant polynucleotide sequences that result from changing no more than a total of 3 percent of the starting coding sequence nucleotides by deletion, insertion, substitution or a combination thereof. Such changes occur within the 5' to 3' portions of the coding sequence of the starting polynucleotide. The polypeptides encoded by such variant polynucleotides may or may not retain the activity of the polypeptide encoded by the polynucleotide of SEQ ID NO:1. For example, such polynucleotides may be employed as probes for the gene comprising the polynucleotide of SEQ ID NO:1, for the polynucleotide of SEQ ID NO:1 or for a redundant polynucleotide which encodes the same polypeptide that is encoded by the polynucleotide having a sequence according to SEQ ID NO:1. However, preferred are the polynucleotides which encode variant polypeptides that retain substantially the same biological function or activity as the mature polypeptide comprising the amino acid sequence encoded by the cDNA of FIG. 1 (SEQ ID NO:2), or that of the amino acid sequence encoded by the polynucleotide of SEQ ID NO:1.

As hereinabove indicated, the polynucleotides may have a coding sequence which is a naturally occurring allelic variant of the coding sequences comprising the coding portion of the polynucleotide sequence shown in FIG. 1 (of SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexahistidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide comprising the amino acid sequence encoded by the cDNA of FIG. 1 (comprising SEQ ID NO:2).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the gene comprising the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and polynucleotides complementary thereto as well as portions thereof, which portions have at least 20, preferably at least 30 consecutive bases and may have at least 50 consecutive bases and to polypeptides encoded by such polynucleotides.

The present invention further relates to polypeptides which have the deduced amino acid sequence as set forth in SEQ ID NO:2, as well as fragments, analogs and derivatives of such polypeptides.

The terms "fragment," "derivative" and "analog" when referring to the mature polypeptides comprising the polypeptide as set forth in SEQ ID NO:2, means polypeptides which retain essentially the same biological function or activity as such polypeptides. Thus, an analog includes a proprotein which can be activated by cleavage of the proprotein portion to produce an active mature polypeptide.

Among the particularly preferred embodiments of the invention in this regard are mature polypeptides comprising the amino acid sequence as set forth in SEQ ID NO:2, variants, analogs, derivatives and fragments thereof, and variants, analogs and derivatives of the fragments. Alternatively, particularly preferred embodiments of the invention in this regard are polypeptides comprising the amino acid sequence of the human slit polypeptide encoded by the cDNA in the deposited clone, variants, analogs, derivatives and fragments thereof, and variants, analogs and derivatives of the fragments.

Further particularly preferred in this regard are variants, analogs, derivatives and fragments, and variants, analogs and derivatives of the fragments, comprising the amino acid sequence of the polypeptide as set forth in SEQ ID NO:2 or as encoded by the cDNA in the deposited clone, in which at least one amino acid residue per each 100 amino acids of the amino sequence is varied by at least one of (a) substituting an amino acid for it, (b) deleting at least one amino acid, (c) inserting at least one new amino acid, or (d) a combination of at least two of (a), (b) and (c). For example, variant polypeptides are obtained whose amino acid sequences are obtained by changing 5 to 10, 1 to 5, 1 to 3, or 1 to 2 amino acid residues per 100 amino acids in that at least one of (i) at least one new amino acid is substituted for an amino acid of SEQ ID NO:2 (or of a fragment of SEQ ID NO:2), (ii) at least one amino acid of SEQ ID NO:2 (or of a fragment of SEQ ID NO:2) is deleted, (ii) at least one new amino acid is inserted into SEQ ID NO:2 (or into a fragment of SEQ ID NO:2), or (iv) a combination of (i), (ii) or (iii). Especially preferred among these are silent substitutions, additions and deletions, which do not alter the properties and activities of such polypeptide as compared to those properties and activities of the human slit polypeptide. Also especially preferred in this regard are conservative substitutions. Most highly preferred are mature polypeptides comprising the amino acid sequence as set forth in SEQ ID NO:2, or of the deposited clone, without substitutions.

The polypeptides of the present invention may be recombinant polypeptides, natural polypeptides or synthetic polypeptides, preferably recombinant polypeptides.

The fragment, derivative or analog of the polypeptides comprising the amino acid sequence set forth in SEQ ID NO:2 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include polypeptides comprising the polypeptide of SEQ ID NO:2 (in particular the mature polypeptide) as well as polypeptides which have at least 70% similarity (preferably at least 70% identity) to the mature polypeptide comprising the amino acid sequence of SEQ ID NO:2, and which have at least 90% similarity (more preferably at least 90% identity) to the mature polypeptide comprising the amino acid sequence of SEQ ID NO:2 and still more preferably at least 95% similarity (still more preferably at least 95% identity) to the mature polypeptide comprising the amino acid sequence of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. For such a determination, two amino acid sequences are compared along a stretch of their sequences, any gap (or gaps) introduced in one sequence to improve the alignment and similarity to the other sequences is counted as spaces of dissimilarity equal to the number of amino acids corresponding to the gap which are present in the second sequence, and the total number of similar amino acids are divided by the total number of amino acids present in the comparison area which counts the spaces of gaps as part of the comparsion area.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site (s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa, 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics for human disease. For example, the polynucleotides and polypeptides encoded by such polynucleotides may also be utilized for in vitro purposes related to scientific research, synthesis of DNA and manufacture of DNA vectors and for designing therapeutics and diagnostics for human disease.

The invention also provides a method for identifying human mesenchymal stem cells by contacting a mixture of mRNA from a cell sample with a polynucleotide unique to human slit and identifying any mRNA which has hybridized with the polynucleotide unique to human slit. In a preferred embodiment the polynucleotide unique to human slit is bound to a solid support. Thus, for example, the identification of slit cDNA enables the slit nucleic acid sequence to be utilized as a diagnostic reagent to identify human MSCs, such as by using gene expression array technology. Labeled (e.g. fluorescent or radiolabeled) mixtures of total cellular mRNA hybridize to cognate elements of slit on a chip based array and allow for the accurate detection of genes specific to MSCs. This technology is described, for example, in Schena, Bioessays, 18(5):427–431 (May 1996) and O'Donnell-Maloney & Little, Genet. Anal., 13(6):151–157 (December 1996).

The polypeptides of the present invention and fragments and analogs and derivatives thereof may be identified by assays which detect MSC proliferation or other activity. Further, assays may be utilized which neutralize the production of the native slit in midline glia cells and subjecting such cells to a polypeptide sequence which is related to the native slit sequence but is different in order to verify the same functionality of polypeptides having both sequences.

This invention is also related to the use of the human slit polypeptide gene as part of a diagnostic assay for detecting diseases or susceptibility to diseases related to the presence of mutations in the human slit polypeptide nucleic acid sequences. Such diseases are related to under expression or overexpression of the human slit polypeptides.

Individuals carrying mutations in the human slit polypeptide gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding human slit polypeptide can be used to identify and analyze human slit polypeptide mutations. For example, deletions and insertions can be detected by a change in size of the amplified product in comparison to the normal genotype. Point mutations can be identified by hybridizing amplified DNA to radiolabeled human slit polypeptide RNA or alternatively, radiolabeled human slit polypeptide antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the slit polypeptide in various tissues since an over-expression or under-expression of the proteins compared to normal control tissue samples may detect the presence of a disease or susceptibility to a disease, for example, reduced blood cell counts or malignancies such as cancers and tumors. Assays used to detect levels of the slit polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the slit polypeptide antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any slit polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to the slit polypeptide. Unattached reporter antibody is then washed out. Peroxidase substrates are then added to the dish and the amount of color developed in a given time period is a measurement of the amount of the slit polypeptide present in a given volume of patient sample when compared against a standard curve.

A competition assay may be employed wherein antibodies specific to the slit polypeptide are attached to a solid support and labeled the slit polypeptide and a sample derived from the host are passed over the solid support and the amount of label detected, for example by liquid scintillation chromatography, can be correlated to a quantity of the slit polypeptide in the sample.

A "sandwich" assay is similar to an ELISA assay. In a "sandwich" assay the slit polypeptide is passed over a solid support and binds to antibody attached to a solid support. A second antibody is then bound to the slit polypeptide. A third antibody which is labeled and specific to the second antibody is then passed over the solid support and binds to the second antibody and an amount can then be quantified.

This invention provides a method for identification of the receptors for the human slit polypeptides. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for the slit polypeptides. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microseguencing. The amino acid sequence obtained from microseguencing would be used to design a set of degenerate oligonucleotide probes to screen a cDNA library to identify the genes encoding the putative receptors.

This invention provides a method of screening compounds to identify agonists and antagonists to the human slit polypeptides of the present invention. An agonist is a compound which has similar biological functions of the polypeptides, while antagonists block such functions. Antagonists and agonists may be identified by the an MSC proliferation assay as is well known in the art.

Examples of potential the slit polypeptide antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription (triple- helix, see Lee et al., Nucl. Acids Res., 6:3073 (1979); Cooney et al, Science, 241:456 (1988); and Dervan et al., Science, 251: 1360 (1991)), thereby preventing transcription and the production of the human slit polypeptide. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the human slit polypeptide.

Another potential human slit antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed in a composition with a pharmaceutically acceptable carrier, e.g., as hereinafter described.

The human slit polypeptides and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the polypeptides will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The human slit polypeptides, and agonists or antagonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an to produce antibodies thereto. These antibodies can be, for example, polyclonal or monoclonal antibodies. The present invention also includes chimeric, single chain, and humanized antibodies, as well as Fab fragments, or the product of an Fab express ion library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Antibodies specific to the polypeptide of the present invention may be employed as a diagnostic to determine elevated or lowered levels of the polypeptide in a sample derived from a host by techniques known in the art. These elevated or lowered levels are indicative of certain disorders which are characterized by such levels of the protein of the present invention and members of its family.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Such antibodies to the polypeptides of the present invention may be utilized to detect the presence or the absence of the polypeptides of the present invention. Thus, they are useful in an assay to verify the successful insertion of the polynucleotides of the present invention (as part of a construct) into a host cell. Thus, the protein encoded by the inserted polynucleotide according to the present invention, when expressed by the transformed host cell, serves as a "marker" for the successful insertion of the polynucleotide that can be detected by an antibody for the marker.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase")

per 0.5 µg of approximately equimolar amounts of the DNA fragments to be ligated.

"Identity" means, as utilized in the context of the present specification and claims, a homology comparison with respect to the degree of sameness between a first sequence and a second sequence (the first sequence may also be referred to as the "reference sequence"). Identity is expressed as the ratio N/D times 100 percent, where N is the number of identical aligned items (bases or amino acids) and D is the sum of the total number of items in the reference sequence and the total individual spaces (corresponding to items in the second sequence) introduced into the reference sequence as a result of its alignment with the second sequence. Further, the alignment by which the N/D ratio of identity is obtained is an alignment which gives essentially the largest possible percentage identity value, i.e., the largest N value (the largest number of aligned sequence items that are identical) and the smallest D value (the smallest number of individual gap spaces introduced into the reference sequence by the alignment). Ascertaining absolutely the highest possible identity value (or best alignment) is not required to report an "essentially largest identity value" since this means in the context of the present application that the percentage identity reported has a certainty deviation that limits any possible increases in the identity value due to an alternative alignment to less than one-half of a percentage point. The sequence alignment utilized to obtain the N/D percentage identity may be performed by a manual method (hand and eye alignment) or by utilizing commercially available alignment software. The parameters of the alignment software may be adjusted until an identity value is obtained which has a certainty that limits any increase in the identity value to less than one-half of a percentage point with respect to the reported identity value.

"At Least X Percent Identity" means, as used in the context of the present specification or claims, a homology comparison with respect to the degree of sameness between a first sequence and a second sequence (the first sequence may also be referred to as the "reference sequence") wherein the degree of sameness is equal to or exceeds the value "X" of the term. The "identity" value (degree of sameness) of this term is expressed as the ratio N/D times 100 percent, where N is the number of identical aligned items (bases or amino acids) and D is the sum of the total number of items in the reference sequence and the total individual spaces (corresponding to items in the second sequence) introduced into the reference sequence as a result of its alignment with the second sequence. If any alignment exists for the second sequence and the reference sequence which results in a sameness value (N/D×100%) that is equal to or greater than the value of "X" in the phrase "at least X percent identity" then the second sequence has "at least X percent identity" with respect to the reference sequence even though it may be possible to align the two sequence in a different manner such that the calculated value is less than X. The sequence alignment utilized to obtain the N/D percentage identity may be performed by a manual method (hand and eye alignment) or by utilizing commercially available alignment software, provided that the "identity" value is calculated as hereinabove described.

Unless otherwise stated, transformation was performed as described in the method of Graham, F. and Van der Eb, A., Virology, 52:456–457 (1973).

The present invention will be further described with reference to the following examples; however, it is to be understood that the present invention is not limited to such examples. All parts or amounts, unless otherwise specified, are by weight.

In order to facilitate understanding of the invention the following examples providing certain frequently occurring methods and/or terms will be described.

EXAMPLE 1

PCR Amplification of Human Slit

The cDNA sequence coding for human slit is obtained from a cDNA library containing it (such as from MSCs or stem cells) and amplified by PCR using the oligonucleotide primers corresponding to the 5' and 3' end sequences of the processed slit nucleic acid sequence. Additional nucleotides corresponding to the slit gene are added to the 5' and 3' end sequences of the processed slit nucleic acid sequence.

For example, the following PCR primers may be utilized for amplification of the cDNA:

5' primer=TCCTCGGGCTCCACGCGTCTT (SEQ ID NO:3), and

3' primer=GGTACATATACGCAGATGGTG (SEQ ID NO:4).

Standard PCR amplification kits are available in the art and may be utilized for such amplification by following the PCR amplification instructions provided therewith.

Isolation of the full-length cDNA may be done utilizing methods standard in the art.

Furthermore, the amplified cDNA may be utilized to produce the polypeptide which it encodes by utilizing methods standard in the art.

EXAMPLE 2

Expression and Purification of Human Slit

The cDNA sequence coding for human slit is obtained from a cDNA library and may be amplified as set forth in Example 1, above.

A. Construction of Expression Plasmid

The full-length hslit cDNA fragment encompassing an EcoR1 site at the 5'-end and engineered to contain a Kpn1 site just before the termination codon was cloned into EcoR1, Kpn1 digested mammalian expression vector, pcDNA3,1/Myc-His/A (Invitrogen, Carlsbad, Calif.) such that the open reading frame of hSlit cDNA was in phase with the C-terminal myc epitope and the polyhistidine tag.

The pcDNA 3.1 vector was utilized in that it is designed for high level expression and purification of recombinant proteins in mammalian cells. The human cytomegalovirus (CMV) promoter was utilized to provide high level expression in a wide range of mammalian cells. The myc epitope and the his tag utilized allow tracking and purification of the expressed protein using commercially available (Invitrogen, Carlsbad, Calif.) anti-myc antibodies and metal-chelating resin, respectively.

B. Transfection of BOSC 23 cells

The human embryonic kidney cell line, BOSC 23, which does not express hSlit, and which can be transfected at a very high efficiency, was used for expression of hSlit. BOSC 23 cells were transiently transfected with vector, or control plasmid, pcDNA3.1/Myc-His/lacZ, or pcDNA3.1/Myc-His/hSlit DNA using the standard calcium phosphate precipitation method. Forty-eight hours post-transfection, total cell lysates were prepared from the transfected and untransfected control cells and analyzed by Western blotting.

C. Western Analysis

Protein content of the cell lysates was estimated using the BCA reagent (Pierce, Rockford, Ill.). Approximately 100 µg of protein from various samples was electrophoresed on a 7.5% SDS-PAGE gel, and electrophoretically transferred to Immobilon PVDF membrane (Milipore, Bedford, Mass.). The protein blot was probed with anti-myc antibodies using ECL detection reagents and protocol (Amersham, UK).

Such procedures are standard in the art. Briefly, the blot was incubated with 5% milk to block non-specific binding sites, followed by incubation with a 1:5000 dilution of anti-myc mouse monoclonal antibodies, and finally incubation with a 1:3000 dilution of anti-mouse Ig linked to horse radish peroxidase. The antibody binding was detected using ECL detection reagents and exposure to X-ray film.

C. Western Analysis Results

The results are shown in the FIG. 4. In FIG. 4, Lane 1 shows the results for untransfected BOSC cells; Lanes 2, 3 and 4, respectively, show (2) BOSC cells transfected with pcDNA3.1/Myc-His/A vector, (3) pcDNA3.1/Myc-His/lacZ and (4) pcDNA3.1/Myc-His/hSlit cDNA.

Numerous modifications and variations of the present invention are possible in light of the above teachings and, therefore, within the scope of the appended claims. Further, the invention may be readily adapted and practiced otherwise than as particularly described.

What is claimed is:

1. An isolated polynucleotide comprising a polynucleotide sequence which is a member selected from the group consisting of:
   (a) a polynucleotide encoding amino acid 2 to 1523 of SEQ ID NO:2; and
   (b) the full complement of (a).

2. The isolated polynucleotide of claim 1 wherein said member is (a).

3. A process for producing a mature slit polypeptide comprising:
   expressing from a recombinant cell containing the polynucleotide of claim 2 the polypeptide encoded by said polynucleotide.

4. The isolated polynucleotide of claim 1 wherein said member is (b).

5. The isolated polynucleotide of claim 1 wherein said polynucleotide sequence is cDNA.

6. A recombinant vector comprising the polynucleotide of claim 5.

7. A recombinant host cell comprising the polynucleotide of claim 5.

8. A method for producing a polypeptide comprising expressing from the recombinant cell of claim 7 the polypeptide encoded by said polynucleotide.

9. The isolated polynucleotide of claim 1 comprising the nucleotide sequence of SEQ ID NO:1.

* * * * *

UNITED STATES PATENT AND TRADEMARK OFFICE
CERTIFICATE OF CORRECTION

PATENT NO.   : 6,342,370 B1
DATED        : January 29, 2002
INVENTOR(S)  : Timothy Connolly and Bhanu Rajput It is certified that error appears in the above-identified patent and that said Letters Patent is hereby corrected as shown below:

<u>Column 13,</u>
Line 61, delete "clones" and insert therefor -- clone --

<u>Column 17,</u>
Line 48, delete "express ion" and insert therefor -- expression --

<u>Column 19,</u>
Line 53, delete "sequence" and insert therefor -- sequences --

Signed and Sealed this

First Day of April, 2003

JAMES E. ROGAN
*Director of the United States Patent and Trademark Office*

SEQUENCE LISTING

<160> NUMBER OF SEQ ID NOS: 5

<210> SEQ ID NO 1
<211> LENGTH: 5176
<212> TYPE: DNA
<213> ORGANISM: Artificial Sequence
<220> FEATURE:
<223> OTHER INFORMATION: Description of Artificial Sequence:cDNA coding
      for the human slit polypeptide of SEQ ID NO:2

<400> SEQUENCE: 1

```
gccggccccg ccgatggagc tgctgttgct gccgccgccg cctcccggag cgccccgctc      60
cgcccgcgcc ccgtgcgcct gagcaccgag ctcgccctcc tccgccgcta actccgccgc     120
ccgctcccca ggccgcccgc gctcccgcg cgcctcctcg ggctccacgc gtcttgcccc      180
gcagaggcag cctcctccag gagcggggcc ctgcacacca tggcccccgg gtgggcaggg     240
gtcggcgccg ccgtgcgcgc ccgcctggcg ctggccttgg cgctggcgag cgtcctgagt     300
gggcctccag ccgtcgcctg ccccaccaag tgtacctgct ccgctgccag cgtggactgc     360
cacgggctgg gcctccgcgc ggttcctcgg ggcatccccc gcaacgctga gcgccttgac     420
ctggacagaa ataatatcac caggatcacc aagatggact cgctgggct caagaacctc     480 cgagtcttgc atctggaaga caaccaggtc agcgtcatcg agagaggcgc cttccaggac     540
ctgaagcagc tagagcgact gcgcctgaac aagaataagc tgcaagtcct tccagaattg     600
cttttccaga gcacgccgaa gctcaccaga ctagatttga gtgaaaacca gatccagggg     660
atcccgagga aggcgttccg cggcatcacc gatgtgaaga acctgcaact ggacaacaac     720
cacatcagct gcattgaaga tggagccttc cgagcgctgc gcgatttgga gatccttacc     780
ctcaacaaca caacatcag tcgcatcctg gtcaccagct caaccacat gccgaagatc     840 cgaactctgc gcctccactc caaccacctg tactgcgact gccacctggc ctggctctcg     900
gattggctgc gacagcgacg gacagttggc cagttcacac tctgcatggc tcctgtgcat     960
ttgaggggct tcaacgtggc ggatgtgcag aagaaggagt acgtgtgccc agcccccac    1020 tcggagcccc catcctgcaa tgccaactcc atctcctgcc cttcgccctg cacgtgcagc    1080
aataacatcg tggactgtcg aggaaagggc ttgatggaga ttcctgccaa cttgccggag    1140
ggcatcgtcg aaatacgcct agaacagaac tccatcaaag ccatccctgc aggagccttc    1200
acccagtaca agaaactgaa gcgaatagac atcagcaaga atcagatatc ggatattgct    1260
ccagatgcct tccagggcct gaaatcactc acatcgctgg tcctgtatgg gaacaagatc    1320
accgagattg ccaaggact gtttgatggg ctggtgtccc tacagctgct cctcctcaat    1380
gccaacaaga tcaactgcct gcgggtgaac acgtttcagg acctgcagaa cctcaacttg    1440
ctctccctgt atgacaacaa gctgcagacc atcagcaagg ggctcttcgc ccctctgcag    1500
```

-continued

```
tccatccaga cactccactt agcccaaaac ccatttgtgt gcgactgcca cttgaagtgg   1560
ctggccgact acctccagga caaccccatc gagacaagcg gggcccgctg cagcagcccg   1620
cgccgactcg ccaacaagcg catcagccag atcaagagca agaagttccg ctgctcaggc   1680
tccgaggatt accgcagcag gttcagcagc gagtgcttca tggacctcgt gtgccccgag   1740
aagtgtcgct gtgagggcac gattgtggac tgctccaacc agaagctggt ccgcatccca   1800
agccacctcc ctgaatatgt caccgacctg cgactgaatg acaatgaggt atctgttctg   1860
gaggccactg gcatcttcaa gaagttgccc aacctgcgga aaataaatct gagtaacaat   1920
aagatcaagg aggtgcgaga gggagctttc gatggagcag ccagcgtgca ggagctgatg   1980
ctgacaggga accagctgga gaccgtgcac gggcgcgtgt tccgtggcct cagtggcctc   2040
aaaaccttga tgctgaggag taacttgatc agctgtgtga gtaatgacac ctttgccggc   2100
ctgagttcgg tgagactgct gtccctctat gacaatcgga tcaccaccat cacccctggg   2160
gccttcacca cgcttgtctc ccctgtccac cataaacctc ctgtccaacc ccttcaactg   2220
caactgccac tggcctggct cggcaagtgg ttgaggaaga gcggatcgt cagtgggaac   2280 cctaggtgcc agaagccatt tttcctcaag gagatcccca tccaggatgt ggccatccag   2340
gacttcacct gtgatggcaa cgaggagagt agttgccagc tgagcccgcg ctgcccggag   2400
cagtgcacct gtatggagac agtggtgcga tgcagcaaca aggggctccg cgccctcccc   2460
agaggcatgc ccaaggatgt gaccgagctg tacctggaag gaaaccacct aacagccgtg   2520
cccagagagc tgtccgccct ccgacacctg acgcttattg acctgagcaa caacagcatc   2580
agcatgctga ccaattacac cttcagtaac atgtctcacc tctccactct gatcctgagc   2640
tacaaccggc tgaggtgcat ccccgtccac gccttcaacg ggctgcggtc cctgcgagtg   2700
ctaaccctcc atggcaatga catttccagc gttcctgaag gctccttcaa cgacctcaca   2760
tctctttccc atctggcgct gggaaccaac ccactccact gtgactgcag tcttcggtgg   2820
ctgtcggagt gggtgaaggc ggggtacaag gagcctggca tcgcccgctg cagtagccct   2880
gagcccatgg ctgacaggct cctgctcacc accccaaccc accgcttcca gtgcaaaggg   2940
ccagtggaca tcaacattgt ggccaaatgc aatgcctgcc tctccagccc gtgcaagaat   3000
aacgggacat gcacccagga ccctgtggag ctgtaccgct gtgcctgccc ctacagctac   3060
aagggcaagg actgcactgt gcccatcaac acctgcatcc agaaccctg tcagcatgga   3120 ggcacctgcc acctgagtga cagccacaag gatgggttca gctgctcctg ccctctgggc   3180
tttgaggggc agcggtgtga gatcaaccca gatgactgtg aggacaacga ctgcgaaaac   3240
aatgccacct gcgtggacgg gatcaacaac tacgtgtgta tctgtccgcc taactacaca   3300
ggtgagctat gcgacgaggt gattgaccac tgtgtgcctg agctgaacct ctgtcagcat   3360
gaggccaagt gcatccccct ggacaaagga ttcagctgcg agtgtgtccc tggctacagc   3420
gggaagctct gtgagacaga caatgatgac tgtgtggccc acaagtgccg ccacggggcc   3480
cagtgcgtgg acacaatcaa tggctacaca tgcacctgcc cccagggctt cagtggaccc   3540
ttctgtgaac ccccccacc catggtccta ctgcagacca gcccatgcga ccagtacgag   3600
tgccagaacg ggcccagtg catcgtggtg cagcaggagc ccacctgccg ctgcccacca   3660
ggcttcgccg gccccagatg cgagaagctc atcactgtca acttcgtggg caaagactcc   3720
tacgtggaac tggcctccgc caaggtccga ccccaggcca catctccct gcaggtggcc   3780 actgacaagg acaacggcat ccttctctac aaaggagaca atgaccccct ggcactggag   3840
```

```
ctgtaccagg gccacgtgcg gctggtctat gacagcgtga gttcccctcc aaccacagtg    3900
tacagtgtgg agacagtgaa tgatgggcag tttcacagtg tggaggtggt gacgctaaac    3960
cagaccctga acttagtagt ggacaaagga actccaaaga gcttggggaa gttccagaag    4020
cagccagcag tgggcatcaa cagccccctc taccttggag catccccac ctccaccggc     4080 ctctccgcct tgcgccaggg cacggaccgg cctctaggcg gcttccacgg atgcatccat    4140
gaggtgcgca tcaacaacga gctgcaggac ttcaaggccc tcccaccaca gtccctgggg    4200
gtgtcaccag gctgcaagtc ctgcaccgtg tgcaagcacg gcctgtgccg ctccgtggag    4260
aaggacagcg tggtgtgcga gtgccgccca ggctggaccg gcccactctg cgatcaggag    4320
gcccgggacc cctgcctcgg ccacagatgc caccatggaa aatgtgtggc aactgggacc    4380
tcatacatgt gcaagtgtgc cgagggctat ggaggggact tgtgtgacaa caagaatgac    4440
tctgccaatg cctgctcagc cttcaagtgt caccatgggc agtgccacat ctcagaccaa    4500
ggggagccct actgcctgtg ccagcccggc tttagcggcg agcactgcca acaagagaat    4560
ccgtgcctgg gaccagtagt ccgagaggtg atccgccgcc agaaaggtta tgcatcatgt    4620
gccacagcct ccaaggtgcc catcatggaa tgtcgtgggg gctgtgggcc ccagtgctgc    4680
cagcccaccc gcagcaagcg gcggaaatac gtcttccagt gcacggacgg ctcctcgttt    4740
gtagaagagg tggagagaca gttagagtgc ggctgcctcg cgtgttccta agcccctgcc    4800
cgcctgcctg ccacctctcg gactccagct tgatggagtt gggacagcca tgtgggaccc    4860
ccgggtgatt cagcatgaag gaaatgaagc tggagaggaa ggtaaagaag aagaatatat    4920
taagtatatt gtaaataaa caaaaatag aacttatttt tattatggaa agtgactatt       4980
ttcatctttt attatataaa tatattacac catctgcgta tatgtaccat atagtgagtt    5040 attttttacca agttttgtgt tgtgtatttg ttgtgttttt aaaaatagct gtttaaaaat    5100
ttaagaaaaa aatagactaa taaaaatgct ttaaaacaaa aggataagaa taaagaatga    5160
tagcctgtct gaggaa                                                    5176
```

<210> SEQ ID NO 2
<211> LENGTH: 1523
<212> TYPE: PRT
<213> ORGANISM: Homo sapiens

<400> SEQUENCE: 2

```
Met Ala Pro Gly Trp Ala Gly Val Gly Ala Ala Val Arg Ala Arg Leu
 1               5                  10                  15

Ala Leu Ala Leu Ala Leu Ala Ser Val Leu Ser Gly Pro Pro Ala Val
            20                  25                  30

Ala Cys Pro Thr Lys Cys Thr Cys Ser Ala Ala Ser Val Asp Cys His
        35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Val Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125
```

-continued

```
Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Val Gly Gln Phe Thr
225                 230                 235                 240

Leu Cys Met Ala Pro Val His Leu Arg Gly Phe Asn Val Ala Asp Val
                245                 250                 255

Gln Lys Lys Glu Tyr Val Cys Pro Ala Pro His Ser Glu Pro Pro Ser
            260                 265                 270

Cys Asn Ala Asn Ser Ile Ser Cys Pro Ser Pro Cys Thr Cys Ser Asn
        275                 280                 285

Asn Ile Val Asp Cys Arg Gly Lys Gly Leu Met Glu Ile Pro Ala Asn
    290                 295                 300

Leu Pro Glu Gly Ile Val Glu Ile Arg Leu Glu Gln Asn Ser Ile Lys
305                 310                 315                 320

Ala Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365

Glu Ile Ala Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Ala Pro Leu Gln Ser Ile Gln Thr Leu
            420                 425                 430

His Leu Ala Gln Asn Pro Phe Val Cys Asp Cys His Leu Lys Trp Leu
        435                 440                 445

Ala Asp Tyr Leu Gln Asp Asn Pro Ile Glu Thr Ser Gly Ala Arg Cys
    450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Ser Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Val Arg Ile Pro Ser
        515                 520                 525

His Leu Pro Glu Tyr Val Thr Asp Leu Arg Leu Asn Asp Asn Glu Val
    530                 535                 540

Ser Val Leu Glu Ala Thr Gly Ile Phe Lys Lys Leu Pro Asn Leu Arg
```

```
                 545                 550                 555                 560

Lys Ile Asn Leu Ser Asn Asn Lys Ile Lys Glu Val Arg Glu Gly Ala
                565                 570                 575

Phe Asp Gly Ala Ala Ser Val Gln Glu Leu Met Leu Thr Gly Asn Gln
                580                 585                 590

Leu Glu Thr Val His Gly Arg Val Phe Arg Gly Leu Ser Gly Leu Lys
                595                 600                 605

Thr Leu Met Leu Arg Ser Asn Leu Ile Ser Cys Val Ser Asn Asp Thr
                610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Pro Val
                645                 650                 655

His His Lys Pro Pro Val Gln Pro Leu Gln Leu Gln Leu Pro Leu Ala
                660                 665                 670

Trp Leu Gly Lys Trp Leu Arg Lys Arg Ile Val Ser Gly Asn Pro
                675                 680                 685

Arg Cys Gln Lys Pro Phe Phe Leu Lys Glu Ile Pro Ile Gln Asp Val
                690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Met Glu Thr Val Val
                725                 730                 735

Arg Cys Ser Asn Lys Gly Leu Arg Ala Leu Pro Arg Gly Met Pro Lys
                740                 745                 750

Asp Val Thr Glu Leu Tyr Leu Glu Gly Asn His Leu Thr Ala Val Pro
                755                 760                 765

Arg Glu Leu Ser Ala Leu Arg His Leu Thr Leu Ile Asp Leu Ser Asn
                770                 775                 780

Asn Ser Ile Ser Met Leu Thr Asn Tyr Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
                820                 825                 830

Asn Asp Ile Ser Ser Val Pro Glu Gly Ser Phe Asn Asp Leu Thr Ser
                835                 840                 845

Leu Ser His Leu Ala Leu Gly Thr Asn Pro Leu His Cys Asp Cys Ser
                850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
                900                 905                 910

Ile Val Ala Lys Cys Asn Ala Cys Leu Ser Ser Pro Cys Lys Asn Asn
                915                 920                 925

Gly Thr Cys Thr Gln Asp Pro Val Glu Leu Tyr Arg Cys Ala Cys Pro
                930                 935                 940

Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
                965                 970                 975
```

-continued

```
Lys Asp Gly Phe Ser Cys Ser Cys Pro Leu Gly Phe Glu Gly Gln Arg
        980                 985                 990
Cys Glu Ile Asn Pro Asp Asp Cys Glu Asp Asn Asp Cys Glu Asn Asn
        995                 1000                1005
Ala Thr Cys Val Asp Gly Ile Asn Asn Tyr Val Cys Ile Cys Pro Pro
    1010                1015                1020
Asn Tyr Thr Gly Glu Leu Cys Asp Glu Val Ile Asp His Cys Val Pro
1025                1030                1035                1040
Glu Leu Asn Leu Cys Gln His Glu Ala Lys Cys Ile Pro Leu Asp Lys
        1045                1050                1055
Gly Phe Ser Cys Glu Cys Val Pro Gly Tyr Ser Gly Lys Leu Cys Glu
        1060                1065                1070
Thr Asp Asn Asp Asp Cys Val Ala His Lys Cys Arg His Gly Ala Gln
        1075                1080                1085
Cys Val Asp Thr Ile Asn Gly Tyr Thr Cys Thr Cys Pro Gln Gly Phe
    1090                1095                1100
Ser Gly Pro Phe Cys Glu His Pro Pro Met Val Leu Leu Gln Thr
1105                1110                1115                1120
Ser Pro Cys Asp Gln Tyr Glu Cys Gln Asn Gly Ala Gln Cys Ile Val
        1125                1130                1135
Val Gln Gln Glu Pro Thr Cys Arg Cys Pro Pro Gly Phe Ala Gly Pro
    1140                1145                1150
Arg Cys Glu Lys Leu Ile Thr Val Asn Phe Val Gly Lys Asp Ser Tyr
        1155                1160                1165
Val Glu Leu Ala Ser Ala Lys Val Arg Pro Gln Ala Asn Ile Ser Leu
    1170                1175                1180
Gln Val Ala Thr Asp Lys Asp Asn Gly Ile Leu Leu Tyr Lys Gly Asp
1185                1190                1195                1200
Asn Asp Pro Leu Ala Leu Glu Leu Tyr Gln Gly His Val Arg Leu Val
            1205                1210                1215
Tyr Asp Ser Val Ser Ser Pro Thr Thr Val Tyr Ser Val Glu Thr
        1220                1225                1230
Val Asn Asp Gly Gln Phe His Ser Val Glu Val Thr Leu Asn Gln
    1235                1240                1245
Thr Leu Asn Leu Val Val Asp Lys Gly Thr Pro Lys Ser Leu Gly Lys
1250                1255                1260
Phe Gln Lys Gln Pro Ala Val Gly Ile Asn Ser Pro Leu Tyr Leu Gly
1265                1270                1275                1280
Gly Ile Pro Thr Ser Thr Gly Leu Ser Ala Leu Arg Gln Gly Thr Asp
        1285                1290                1295
Arg Pro Leu Gly Gly Phe His Gly Cys Ile His Glu Val Arg Ile Asn
        1300                1305                1310
Asn Glu Leu Gln Asp Phe Lys Ala Leu Pro Pro Gln Ser Leu Gly Val
        1315                1320                1325
Ser Pro Gly Cys Lys Ser Cys Thr Val Cys Lys His Gly Leu Cys Arg
    1330                1335                1340
Ser Val Glu Lys Asp Ser Val Val Cys Glu Cys Arg Pro Gly Trp Thr
1345                1350                1355                1360
Gly Pro Leu Cys Asp Gln Glu Ala Arg Asp Pro Cys Leu Gly His Arg
            1365                1370                1375
Cys His His Gly Lys Cys Val Ala Thr Gly Thr Ser Tyr Met Cys Lys
        1380                1385                1390
```

-continued

```
Cys Ala Glu Gly Tyr Gly Gly Asp Leu Cys Asp Asn Lys Asn Asp Ser
        1395                1400                1405

Ala Asn Ala Cys Ser Ala Phe Lys Cys His His Gly Gln Cys His Ile
    1410                1415                1420

Ser Asp Gln Gly Glu Pro Tyr Cys Leu Cys Gln Pro Gly Phe Ser Gly
1425                1430                1435                1440

Glu His Cys Gln Gln Glu Asn Pro Cys Leu Gly Gln Val Val Arg Glu
                1445                1450                1455

Val Ile Arg Arg Gln Lys Gly Tyr Ala Ser Cys Ala Thr Ala Ser Lys
            1460                1465                1470

Val Pro Ile Met Glu Cys Arg Gly Gly Cys Gly Pro Gln Cys Cys Gln
        1475                1480                1485

Pro Thr Arg Ser Lys Arg Arg Lys Tyr Val Phe Gln Cys Thr Asp Gly
    1490                1495                1500

Ser Ser Phe Val Glu Glu Val Glu Arg His Leu Glu Cys Gly Cys Leu
1505                1510                1515                1520

Ala Cys Ser

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:PCR primer
      for amplification of cDNA of SEQ ID NO:1

<400> SEQUENCE: 3
tcctcgggct ccacgcgtct t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:PCR primer
      for amplification of cDNA of SEQ ID NO:1

<400> SEQUENCE: 4
ggtacatata cgcagatggt g                                              21

<210> SEQ ID NO 5
<211> LENGTH: 1480
<212> TYPE: PRT
<213> ORGANISM: Drosophila melanogaster

<400> SEQUENCE: 5

Met Ala Ala Pro Ser Arg Thr Thr Leu Met Pro Pro Phe Arg Leu
  1               5                  10                  15

Gln Leu Arg Leu Leu Ile Leu Pro Ile Leu Leu Leu Arg His Asp
             20                  25                  30

Ala Val His Ala Glu Pro Tyr Ser Gly Phe Gly Ser Ser Ala Val
         35                  40                  45

Ser Ser Gly Gly Leu Gly Ser Val Gly Ile His Ile Pro Gly Gly Gly
     50                  55                  60

Val Gly Val Ile Thr Glu Ala Arg Cys Pro Arg Val Cys Ser Cys Thr
 65                  70                  75                  80

Gly Leu Asn Val Asp Cys Ser His Arg Gly Leu Thr Ser Val Pro Arg
                 85                  90                  95

Lys Ile Ser Ala Asp Val Glu Arg Leu Glu Leu Gln Gly Asn Asn Leu
```

```
                    100                 105                 110
Thr Val Ile Tyr Glu Thr Asp Phe Gln Arg Leu Thr Lys Leu Arg Met
            115                 120                 125

Leu Gln Leu Thr Asp Asn Gln Ile His Thr Ile Glu Arg Asn Ser Phe
    130                 135                 140

Gln Asp Leu Val Ser Leu Glu Arg Leu Asp Ile Ser Asn Asn Val Ile
145                 150                 155                 160

Thr Thr Val Gly Arg Val Phe Lys Gly Ala Gln Ser Leu Arg Ser
                165                 170                 175

Leu Gln Leu Asp Asn Asn Gln Ile Thr Cys Leu Asp Glu His Ala Phe
            180                 185                 190

Lys Gly Leu Val Glu Leu Glu Ile Leu Thr Leu Asn Asn Asn Asn Leu
                195                 200                 205

Thr Ser Leu Pro His Asn Ile Phe Gly Gly Leu Gly Arg Leu Arg Ala
    210                 215                 220

Leu Arg Leu Ser Asp Asn Pro Phe Ala Cys Asp Cys His Leu Ser Trp
225                 230                 235                 240

Leu Ser Arg Phe Leu Arg Ser Ala Thr Arg Leu Ala Pro Tyr Thr Arg
                245                 250                 255

Cys Gln Ser Pro Ser Gln Leu Lys Gly Gln Asn Val Ala Asp Leu His
            260                 265                 270

Asp Gln Glu Phe Lys Cys Ser Gly Leu Thr Glu His Ala Pro Met Glu
        275                 280                 285

Cys Gly Ala Glu Asn Ser Cys Pro His Pro Cys Arg Cys Ala Asp Gly
    290                 295                 300

Ile Val Asp Cys Arg Glu Lys Ser Leu Thr Ser Val Pro Val Thr Leu
305                 310                 315                 320

Pro Asp Asp Thr Thr Asp Val Leu Leu Glu Gln Asn Phe Ile Thr Glu
                325                 330                 335

Leu Pro Pro Lys Ser Phe Ser Ser Phe Arg Arg Leu Arg Arg Ile Asp
            340                 345                 350

Leu Ser Asn Asn Asn Ile Ser Arg Ile Ala His Asp Ala Leu Ser Gly
        355                 360                 365

Leu Lys Gln Leu Thr Thr Leu Val Leu Tyr Gly Asn Lys Ile Lys Asp
    370                 375                 380

Leu Pro Ser Gly Val Phe Lys Gly Leu Gly Ser Leu Arg Leu Leu Leu
385                 390                 395                 400

Leu Asn Ala Asn Glu Ile Ser Cys Ile Arg Lys Asp Ala Phe Arg Asp
                405                 410                 415

Leu His Ser Leu Ser Leu Leu Ser Leu Tyr Asp Asn Asn Ile Gln Ser
            420                 425                 430

Leu Ala Asn Gly Thr Phe Asp Ala Met Lys Ser Met Lys Thr Val His
        435                 440                 445

Leu Ala Lys Asn Pro Phe Ile Cys Asp Cys Asn Leu Arg Trp Leu Ala
    450                 455                 460

Asp Tyr Leu His Lys Asn Pro Ile Glu Thr Ser Gly Ala Arg Cys Glu
465                 470                 475                 480

Ser Pro Lys Arg Met His Arg Arg Ile Glu Ser Leu Arg Glu Glu
                485                 490                 495

Lys Phe Lys Cys Ser Trp Gly Glu Leu Arg Met Lys Leu Ser Gly Glu
            500                 505                 510

Cys Arg Met Asp Ser Asp Cys Pro Ala Met Cys His Cys Glu Gly Thr
        515                 520                 525
```

```
Thr Val Asp Cys Thr Gly Arg Arg Leu Lys Glu Ile Pro Arg Asp Ile
    530                 535                 540
Pro Leu His Thr Thr Glu Leu Leu Asn Asp Asn Glu Leu Gly Arg
545                 550                 555                 560
Ile Ser Ser Asp Gly Leu Phe Gly Arg Leu Pro His Leu Val Lys Leu
                565                 570                 575
Glu Leu Lys Arg Asn Gln Leu Thr Gly Ile Glu Pro Asn Ala Phe Glu
            580                 585                 590
Gly Ala Ser His Ile Gln Glu Leu Gln Leu Gly Glu Asn Lys Ile Lys
        595                 600                 605
Glu Ile Ser Asn Lys Met Phe Leu Gly Leu His Gln Leu Lys Thr Leu
    610                 615                 620
Asn Leu Tyr Asp Asn Gln Ile Ser Cys Val Met Pro Gly Ser Phe Glu
625                 630                 635                 640
His Leu Asn Ser Leu Thr Ser Leu Asn Leu Ala Ser Asn Pro Phe Asn
                645                 650                 655
Cys Asn Cys His Leu Ala Trp Phe Ala Glu Cys Val Arg Lys Lys Ser
                660                 665                 670
Leu Asn Gly Gly Ala Ala Arg Cys Gly Ala Pro Ser Lys Val Arg Asp
            675                 680                 685
Val Gln Ile Lys Asp Leu Pro His Ser Glu Phe Lys Cys Ser Ser Glu
690                 695                 700
Asn Ser Glu Gly Cys Leu Gly Asp Gly Tyr Cys Pro Pro Ser Cys Thr
705                 710                 715                 720
Cys Thr Gly Thr Val Val Ala Cys Ser Arg Asn Gln Leu Lys Glu Ile
                725                 730                 735
Pro Arg Gly Ile Pro Ala Glu Thr Ser Glu Leu Tyr Leu Glu Ser Asn
            740                 745                 750
Glu Ile Glu Gln Ile His Tyr Glu Arg Ile Arg His Leu Arg Ser Leu
    755                 760                 765
Thr Arg Leu Asp Leu Ser Asn Asn Gln Ile Thr Ile Leu Ser Asn Tyr
    770                 775                 780
Thr Phe Ala Asn Leu Thr Lys Leu Ser Thr Leu Ile Ile Ser Tyr Asn
785                 790                 795                 800
Lys Leu Gln Cys Leu Gln Arg His Ala Leu Ser Gly Leu Asn Asn Leu
                805                 810                 815
Arg Val Val Ser Leu His Gly Asn Arg Ile Ser Met Leu Pro Glu Gly
            820                 825                 830
Ser Phe Glu Asp Leu Lys Ser Leu Thr His Ile Ala Leu Gly Ser Asn
    835                 840                 845
Pro Leu Tyr Cys Asp Cys Gly Leu Lys Trp Phe Ser Asp Trp Ile Lys
    850                 855                 860
Leu Asp Tyr Val Glu Pro Gly Ile Ala Arg Cys Ala Glu Pro Glu Gln
865                 870                 875                 880
Met Lys Asp Lys Leu Ile Leu Ser Thr Pro Ser Ser Ser Phe Val Cys
                885                 890                 895
Arg Gly Arg Val Arg Asn Asp Ile Leu Ala Lys Cys Asn Ala Cys Phe
            900                 905                 910
Glu Gln Pro Cys Gln Asn Gln Ala Gln Cys Val Ala Leu Pro Gln Arg
    915                 920                 925
Glu Tyr Gln Cys Leu Cys Gln Pro Gly Tyr His Gly Lys His Cys Glu
    930                 935                 940
```

-continued

```
Phe Met Ile Asp Ala Cys Tyr Gly Asn Pro Cys Arg Asn Asn Ala Thr
945                 950                 955                 960

Cys Thr Val Leu Glu Glu Gly Arg Phe Ser Cys Gln Cys Ala Pro Gly
                965                 970                 975

Tyr Thr Gly Ala Arg Cys Glu Thr Asn Ile Asp Asp Cys Leu Gly Glu
                980                 985                 990

Ile Lys Cys Gln Asn Asn Ala Thr Cys Ile Asp Gly Val Glu Ser Tyr
            995                 1000                1005

Lys Cys Glu Cys Gln Pro Gly Phe Ser Gly Glu Phe Cys Asp Thr Lys
        1010                1015                1020

Ile Gln Phe Cys Ser Pro Glu Phe Asn Pro Cys Ala Asn Cys Ala Lys
1025                1030                1035                1040

Cys Met Asp His Phe Thr His Tyr Ser Cys Asp Cys Gln Ala Gly Phe
                1045                1050                1055

His Gly Thr Asn Cys Thr Asp Asn Ile Asp Asp Cys Gln Asn His Met
                1060                1065                1070

Cys Gln Asn Gly Gly Thr Cys Val Asp Gly Ile Asn Asp Tyr Gln Cys
            1075                1080                1085

Arg Cys Pro Asp Asp Tyr Thr Gly Lys Tyr Cys Glu Gly His Asn Met
        1090                1095                1100

Ile Ser Met Met Tyr Pro Gln Thr Ser Pro Cys Gln Asn His Glu Cys
1105                1110                1115                1120

Lys His Gly Val Cys Phe Gln Pro Asn Ala Gln Gly Ser Asp Tyr Leu
                1125                1130                1135

Cys Arg Cys His Pro Gly Tyr Thr Gly Lys Trp Cys Glu Tyr Leu Thr
                1140                1145                1150

Ser Ile Ser Phe Val His Asn Asn Ser Phe Val Glu Leu Glu Pro Leu
            1155                1160                1165

Arg Thr Arg Pro Glu Ala Asn Val Thr Ile Val Phe Ser Ser Ala Glu
        1170                1175                1180

Gln Asn Gly Ile Leu Met Tyr Asp Gly Gln Asp Ala His Leu Ala Val
1185                1190                1195                1200

Glu Leu Phe Asn Gly Arg Ile Arg Val Ser Tyr Asp Val Gly Asn His
                1205                1210                1215

Pro Val Ser Thr Asn Tyr Ser Phe Glu Met Val Ala Asp Gly Lys Tyr
                1220                1225                1230

His Ala Val Glu Leu Leu Ala Ile Lys Lys Asn Phe Thr Leu Arg Val
            1235                1240                1245

Asp Arg Gly Leu Ala Arg Ser Ile Ile Asn Glu Gly Ser Asn Asp Tyr
        1250                1255                1260

Leu Lys Leu Thr Thr Pro Met Phe Leu Gly Gly Leu Pro Val Asp Pro
1265                1270                1275                1280

Ala Gln Gln Ala Tyr Lys Asn Trp Gln Ile Arg Asn Leu Thr Ser Phe
                1285                1290                1295

Lys Gly Cys Met Lys Glu Val Trp Ile Asn His Lys Leu Val Asp Phe
                1300                1305                1310

Gly Asn Ala Gln Arg Gln Gln Lys Ile Thr Pro Gly Cys Ala Leu Leu
            1315                1320                1325

Glu Gly Glu Gln Gln Glu Glu Glu Asp Asp Glu Gln Asp Phe Met Asp
        1330                1335                1340

Glu Thr Pro His Ile Lys Glu Glu Pro Val Asp Pro Cys Leu Glu Asn
1345                1350                1355                1360

Lys Cys Arg Arg Gly Ser Arg Cys Val Pro Asn Ser Asn Ala Arg Asp
```

-continued

```
                    1365                    1370                    1375
Gly Tyr Gln Cys Lys Cys Lys His Gly Gln Arg Gly Arg Tyr Cys Asp
            1380                    1385                    1390

Gln Gly Glu Gly Ser Thr Glu Pro Pro Thr Val Thr Ala Ala Ser Thr
        1395                    1400                    1405

Cys Arg Lys Glu Gln Val Arg Glu Tyr Tyr Thr Glu Asn Asp Cys Arg
    1410                    1415                    1420

Ser Arg Gln Pro Leu Lys Tyr Ala Lys Cys Val Gly Cys Gly Asn
1425                    1430                    1435                    1440

Gln Cys Cys Ala Ala Lys Ile Val Arg Arg Lys Val Arg Met Val
                1445                    1450                    1455

Cys Ser Asn Asn Arg Lys Tyr Ile Lys Asn Leu Asp Ile Val Arg Lys
            1460                    1465                    1470

Cys Gly Cys Thr Lys Lys Cys Tyr
        1475                1480
```